(12) United States Patent
Fredriksson et al.

(10) Patent No.: US 8,632,836 B2
(45) Date of Patent: Jan. 21, 2014

(54) NANOSURFACE

(75) Inventors: Anette Fredriksson, Västra Frölunda (SE); Ingela Petersson, Göteborg (SE)

(73) Assignee: Astra Tech AB, Molndal (SE)

( * ) Notice: Subject to any disclaimer, the term of this patent is extended or adjusted under 35 U.S.C. 154(b) by 106 days.

(21) Appl. No.: 12/298,884

(22) PCT Filed: Jul. 8, 2008

(86) PCT No.: PCT/EP2008/058860
§ 371 (c)(1),
(2), (4) Date: Jan. 21, 2009

(87) PCT Pub. No.: WO2009/007373
PCT Pub. Date: Jan. 15, 2009

(65) Prior Publication Data
US 2010/0173264 A1     Jul. 8, 2010

(30) Foreign Application Priority Data
Jul. 9, 2007 (EP) .................................. 07112076

(51) Int. Cl.
*B05D 3/10* (2006.01)
*C25C 3/00* (2006.01)

(52) U.S. Cl.
USPC .......... 427/2.1; 427/2.24; 427/2.25; 427/307; 427/337; 216/83; 216/96; 216/100; 216/108; 216/109

(58) Field of Classification Search
USPC ............... 427/2.1, 2.24, 2.26, 2.27, 331, 337, 427/307, 2.25; 216/83, 96, 100, 101, 216/108–109
See application file for complete search history.

(56) References Cited

U.S. PATENT DOCUMENTS 4,882,196 A * 11/1989 Shimamune et al. ........ 427/2.27
5,141,576 A    8/1992 Shimamune et al.
5,356,516 A    10/1994 Ashby et al.

(Continued)

FOREIGN PATENT DOCUMENTS

CN    1237945 C    5/1975
EP    0401793 A1   12/1990

(Continued)

OTHER PUBLICATIONS

Yi, Ji-Hyun, et al., "Characterization of a bioactive nanotextured surface created by controlled chemical oxidation of titanium," Surface Science, pp. 4613-4621 (2006).

Zinger, O., et al., "Differential regulation of osteoblasts by substrate microstructural features," Biomaterials, vol. 26, pp. 1837-1847 (2005).

(Continued)

*Primary Examiner* — Cachet Sellman
(74) *Attorney, Agent, or Firm* — Birch, Stewart, Kolasch & Birch, LLP

(57) ABSTRACT

The invention relates to a method for modification of a biocompatible component comprising the steps of a) providing a biocompatible component at least partly covered by metallic oxide; and b) treating at least a part of said component, which part is covered by said metallic oxide, with an aqueous composition comprising oxalic acid; whereby a modified metallic oxide is obtained. The invention also relates to a biocompatible component comprising a substrate having a surface comprising a) a microstructure comprising pits separated by plateus and/or ridges; and b) a primary nanostructure being superimposed on said microstructure, said primary nanostructure comprising depressions arranged in a wave-like formation.

27 Claims, 38 Drawing Sheets

(56) References Cited

U.S. PATENT DOCUMENTS

| | | | |
|---|---|---|---|
| 5,603,338 A * | 2/1997 | Beaty | 128/898 |
| 5,824,651 A | 10/1998 | Nanci et al. | |
| 5,863,201 A | 1/1999 | Lazzara et al. | |
| 5,876,453 A * | 3/1999 | Beaty | 433/201.1 |
| 5,989,027 A | 11/1999 | Wagner et al. | |
| 6,069,295 A | 5/2000 | Leitao et al. | |
| 6,110,204 A | 8/2000 | Lazarov et al. | |
| 6,183,570 B1 | 2/2001 | Kawaguchi et al. | |
| 6,491,723 B1 | 12/2002 | Beaty | |
| 6,652,765 B1 | 11/2003 | Beaty | |
| 6,969,474 B2 | 11/2005 | Beaty | |
| 7,048,541 B2 | 5/2006 | Hall et al. | |
| 7,169,317 B2 | 1/2007 | Beaty | |
| 2001/0052468 A1* | 12/2001 | Jacobo et al. | 205/208 |
| 2002/0016635 A1 | 2/2002 | Despres et al. | |
| 2002/0153348 A1* | 10/2002 | Say et al. | 216/56 |
| 2002/0198601 A1 | 12/2002 | Bales et al. | |
| 2003/0108659 A1* | 6/2003 | Bales et al. | 427/2.24 |
| 2004/0148031 A1 | 7/2004 | Beaty | |
| 2004/0153154 A1* | 8/2004 | Dinkelacker | 623/16.11 |
| 2004/0167632 A1 | 8/2004 | Wen et al. | |
| 2004/0167633 A1 | 8/2004 | Wen et al. | |
| 2004/0265780 A1 | 12/2004 | Robb et al. | |
| 2005/0019365 A1 | 1/2005 | Frauchiger et al. | |
| 2005/0031663 A1 | 2/2005 | Larsson et al. | |
| 2005/0049716 A1 | 3/2005 | Wagener et al. | |
| 2005/0119758 A1 | 6/2005 | Alexander et al. | |
| 2005/0161440 A1* | 7/2005 | Ellingsen et al. | 216/109 |
| 2006/0216358 A1* | 9/2006 | Hansen et al. | 424/603 |
| 2006/0289388 A1* | 12/2006 | Yang et al. | 216/96 |
| 2006/0292062 A1 | 12/2006 | Hojo et al. | |
| 2007/0110890 A1 | 5/2007 | Berckmans et al. | |
| 2007/0112353 A1 | 5/2007 | Berckmans et al. | |

FOREIGN PATENT DOCUMENTS

| | | |
|---|---|---|
| EP | 0493326 | 7/1992 |
| EP | 0746273 B1 | 12/1996 |
| EP | 0806211 B1 | 11/1997 |
| EP | 0806212 B1 | 11/1997 |
| EP | 0810889 B1 | 12/1997 |
| EP | 0887179 B1 | 12/1998 |
| EP | 1352665 A1 | 10/2003 |
| EP | 1440669 B1 | 7/2004 |
| EP | 1448908 B1 | 8/2004 |
| EP | 1449544 A1 | 8/2004 |
| EP | 1449544 A1 * | 8/2004 |
| EP | 1771125 | 4/2007 |
| JP | H03-146679 | 6/1991 |
| JP | H04-028374 | 1/1992 |
| WO | WO-2006004297 A1 | 1/2006 |
| WO | WO-2006022878 A1 | 3/2006 |
| WO | WO-2006091582 A2 | 8/2006 |
| WO | WO-2006096475 A1 | 9/2006 |
| WO | WO-2006102347 A2 | 9/2006 |
| WO | WO-2007059038 A2 | 5/2007 |

OTHER PUBLICATIONS

Li, Dehua, et al., "Effects of a Modified Sandblasting Surface Treatment on Topographic and Chemical Properties of Titanium Surface," Implant Dentistry, vol. 10, No. 1, pp. 59-63 (2001).

Bagno, A., et al., "Surface treatments and roughness properties of Ti-based biomaterials," J. Mat. Science: Mat. in Med., vol. 15, pp. 935-949 (2004).

Li, Long-Hao, et al., "Improved biological performance of Ti implants due to surface modification by micro-arc oxidation," Biomaterials, vol. 25, pp. 2867-2875 (2004).

Office Action issued in corresponding Japanese Application No. 2010-515496 on Jan. 29, 2013.

Albrektsson et al., "An ultrastructural characterization of the interface between bone and sputtered titanium or stainless steel surfaces," Biomaterials, 1986, vol. 7, pp. 201-205.

Albrektsson et al., "Interface analysis of titanium and zirconium bone implants," Biomaterials, 1985, vol. 6, pp. 97-101.

Albrektsson et al., "Osseointegrated titanium implants. Requirements for ensuring a long-lasting, direct bone anchorage in man", Acta Orthop Scand, 1981, vol. 52(2), pp. 155-170.

Albrektsson et al., "Ultrastructural analysis of the interface zone of titanium and gold implants," Clinical Applications of Biomaterials, 1982, vol. 4, pp. 167-177.

Anselme, "Osteoblast adhesion on biomaterials," Biomaterials, Apr. 2000, vol. 21(7), pp. 667-681.

Australian Office Action issued in Australian Application No. 2008274303; Jan. 8, 2013.

Bershadsky et al., "Adhesion-mediated mechanosensitivity: a time to experiment, and a time to theorize," Current Opinion in Cell Biology, 2006, vol. 18(5), pp. 472-481.

Branemark et al., "Osseointegrated Implants in the Treatment of the Edentulous Jaw. Experience from a 10-year period," Scandinavian Journal of Plastic and Reconstructive Surgery, 1977, vol. 16, pp. 1-132, Stockholm, Sweden.

Cooper et al., "A multicenter 12-month evaluation of single-tooth implants restored 3 weeks after 1-stage surgery," The International Journal of Oral & Maxillofacial Implants, 2001, vol. 16(2), pp. 182-192.

English translation of Chinese office action issued in Chinese Application No. 200880024004.6; Mar. 28, 2013.

Esposito, "Titanium In Medicine," Material Science, Surface Science, Engineering, Biological Resources & Medical Application, 2001, pp. 836-837, Springer-Verlag.

Extended European Search Report issued in European Application No. 10194575.6; Mar. 22, 2011.

Extended European Search Report issued in European Application No. 12179573.6; Nov. 27, 2012.

Hansson et al. "Structural aspects of the interface between issue and titanium implants," Journal of Prosthetic Dentistry, Jul. 1983, vol. 50, pp. 108-113.

Johansson et al., "A removal torque and histomorphometric study of commercially pure niobium and titanium implants in rabbit bone," Clinical Oral Implants Research, 1991, vol. 2, pp. 24-29.

Johansson et al., "Qualitative interfacial study between bone and tantalum, niobium or commercially pure titanium," Biomaterials, May 1990, vol. 11, pp. 277-280.

Johansson et al., "Ultrastructural differences of the interface zone between bone and Ti 6A1 4V or commercially pure titanium," Journal of Biomedical Engineering, Jan. 1989, vol. 11, pp. 3-8.

Kieswetter et al., "Surface roughness modulates the local production of growth factors and cytokines by osteoblast-like MG-63 cells," Journal of Biomedical Materials Research, Sep. 1996, vol. 32(1), pp. 55-63, 1996.

Kokubo et al., "How useful is SBF in predicting in vivo bone bioactivity?" Biomaterials, 2006, vol. 27, pp. 2907-2915.

Kokubo et al., "Solutions able to reproduce in vivo surface-structure changes in bioactive glass-ceramic A-W3," Journal of Biomedical Materials Research, 1990, vol. 24, pp. 721-734.

Martin et al., "Proliferation, differentiation, and protein synthesis of human osteoblast-like cells (MG63) cultured on previously used titanium surfaces," Clinical Oral Implants Research, Mar. 1996, vol. 7(1), pp. 27-37.

Oyane et al., "Preparation and assesment of revised simulated body fluids," Journal of Biomedical Materials Research, 2003, vol. 65(A), pp. 188-195.

Sennerby et al., "Early tissue response to titanium implants inserted in rabbit cortical bone, Part II: Ultrastructural observations," Journal of Materials Science: Materials in Medicine, 1993, vol. 4, pp. 494-502.

Sennerby et al., "Structure of the bone-titanium interface in retrieved clinical oral implants," Clinical Oral Implants Research, 1991, vol. 2, pp. 103-111.

Sennerby et al., "Ultrastructure of the bone-titanium interface in rabbits," Journal of Materials Science: Materials in Medicine, 1992, vol. 3, pp. 262-271.

* cited by examiner

Removal torque test after 6 weeks of implantation into rabbit tibia

NANOSURFACE

This Application is the National Phase Under 35 U.S.C. §371 of PCT International Application No. PCT/EP2008/058860 which has an International filing date of Jul. 8, 2008, which claims priority to European Application No. EP 07112076.0 filed on Jul. 9, 2007. The entire contents of all applications listed above are hereby incorporated by reference.

FIELD OF THE INVENTION

The present invention relates to a biocompatible component which has improved properties for implantation into bone tissue.

TECHNICAL BACKGROUND

For implanting orthopaedic or dental implants, generally metallic implants, into bone tissue, a one-stage procedure is nowadays often used. In the one-stage procedure, a first implant part, such as a dental fixture, is generally surgically placed into the bone tissue, and a healing cap or a secondary implant part, such as an abutment, is then attached to the first implant part directly after the surgical operation. The soft tissue is then allowed to heal around the healing cap or the secondary implant part. When a healing cap is used, the cap is removed after a few weeks or months without any surgical procedure, and secondary implant parts, such as an abutment and a provisional crown, are attached to the first implant part. The one-stage procedure is for instance described in L Cooper et al: "A multicenter 12month evaluation of single-tooth implants restored 3 weeks after 1-stage surgery", The International Journal of Oral & Maxillofacial Implants, Vol 16, No 2 (2001).

The two-stage procedure, which in some dental cases still is preferable, generally involves in a first stage surgically placing a first implant part, such as a dental fixture, into the bone tissue, where it is allowed to rest unloaded and immobile for a healing period, often of three months or more, in order to allow the bone tissue to grow onto the implant surface to permit the implant to be well attached to the bone tissue, the cut in the soft tissue covering the implant site being allowed to heal over the implant. In a second stage, the soft tissue covering the implant is opened and secondary implant parts, such as a dental abutment and/or a restoration tooth, are attached to the first implant part, such as said fixture, forming the final implant structure. This procedure is for instance described by Brånemark et al: "Osseointegrated Implants in the Treatment of the Edentulous Jaw, Experience from a 10-year period", Almquist & Wiksell International, Stockholm, Sweden.

However, the fact that the implant not should be loaded during the healing period means that the secondary implant parts may not be attached to the first implant part and/or used during the healing period. In view of the discomfort associated with this, it is desirable to minimize the time period necessary for the above-mentioned first stage or even perform the entire implantation procedure in a single operation, i.e. to use the one-stage procedure.

For some patients, it might be considered better to wait at least three months before functionally loading the implant, both for one- and two-stage procedures. However, an alternative using the one-stage procedure is to put the implant in function directly after implantation (immediate loading) or a few weeks after implantation (early loading). These procedures are, for instance, described by D M Esposito, pp 836-837, in "Titanium in Medicine, Material Science, Surface Science, Engineering, Biological Responses and Medical Application", Springer-Verlag (2001).

It is essential that the implant establishes a sufficient stability and bond between implant and bone tissue to enable the above disclosed immediate or early loading of the implant. It shall also be noted that an immediate or early loading of the implant may be beneficial to bone formation.

Some of the metals or alloys, such as titanium, zirconium, hafnium, tantalum, niobium, or alloys thereof, that are used for bone implants are capable of forming a relatively strong bond with the bone tissue, a bond which may be as strong as the bone tissue per se, and sometimes even stronger. The most notable example of this kind of metallic implant material is titanium and alloys of titanium whose properties in this respect have been known since about 1950. The bond between the metal and the bone tissue has been termed "osseointegration" (Albrektsson T, Brånemark P I, Hansson H A, Lindström J, "Osseointegrated titanium implants. Requirements for ensuring a long-lasting, direct bone anchorage in man", Acta Orthop Scand, 52:155-170 (1981)).

It may be noted that in contact with oxygen, titanium, zirconium, hafnium, tantalum, niobium and their alloys are instantaneously covered with a native oxide. This native oxide on titanium implants mainly consist of titanium(IV) dioxide ($TiO_2$) with minor amounts of $Ti_2O_3$, TiO and $Ti_3O_4$.

Although the bond between the (oxidised) metal, e.g. titanium, and the bone tissue may be comparatively strong, it is desirable to enhance this bond.

There are to date several methods for treating metallic implants in order to obtain a better attachment of the implant, and thus improved osseointegration. Some of these involve altering the morphology of the implant, for example by creating irregularities on the implant surface in order to increase the surface roughness in comparison to an untreated surface. It is believed that an increased surface roughness, which gives a larger contact and attachment area between the implant and the bone tissue, provides a better mechanical retention and strength between implant and bone. It is well-known within the art that a surface roughness can be provided by, for example, plasma spraying, blasting or acid etching.

Furthermore, it is known that osteoblasts, i.e, bone-forming cells, sense and react to multiple chemical and physical features of the underlying surface. Formation of bone at an implant surface requires the differentiation of precursor cells into secretory osteoblasts to produce unmineralised extracellular matrix (ECM), and the subsequent calcification of this matrix, as described in for instance Anselme K, "Osteoblast adhesion on biomaterials", Biomaterials 21, 667-681 (2000).

Alteration of the chemical properties of the implant surface has frequently been used for achieving a better attachment of the implant to the bone tissue. Several methods involve the application of a layer of ceramic material, such as hydroxyapatite, on the implant surface in order to improve the bonding of the implant to bone since hydroxyapatite is chemically related to bone. U.S. Pat. No. 7,169,317 (Beaty) discloses a method for preparing the surface of a bone implant which comprises the removal of the native oxide from the implant surface, acid etching or otherwise treating the resulting implant surface to produce a substantially uniform surface roughness, and depositing discrete particles of a bone-growth enhancing material such as hydroxyapatite, bone minerals and bone morphogenic proteins thereon. The etching and deposition steps are preferably performed in the absence of unreacted oxygen by using an inert atmosphere.

A common disadvantage with coatings comprising hydroxyapatite is, however, that they may be brittle and may flake or break off from the implant surface due to a stronger bond being formed between the bone and coating than between the coating and the implant, which may lead to an ultimate failure of the implant. Regarding the use of protein coatings, there are additional aspects to consider. Due to the chemical nature of proteins, a surface having a protein coating may require specific sterilisation and storage conditions in order to maintain its biological activity. In addition, host tissue response (e.g. immunological response) to biomolecules such as proteins may be unpredictable. Another disadvantage of the method of U.S. Pat. No. 7,169,317 is the requirement for a surface free of oxide, considering that working in an inert atmosphere is inconvenient and requires specialized equipment.

US 2007/01100890 and related applications US 2007/0112353 and WO 2007/050938 (Berckmans III et al) aim at solving the problem of poor adherence of a ceramic coating to the implant and disclose a method of depositing discrete nanoparticles on a roughened implant surface through a process of exposing the implant surface to a solution comprising 2-methoxyethanol solvent and hydroxyapatite (HA) nanocrystals, e.g. in the form of a colloid. The HA nanocrystals are deposited to form a nanostructure which is intended to promote the osseointegration of the implant. However, one negative aspect of this method is the formulation of the nanocrystal-containing composition requiring organic solvents, which may be undesirable due to the risk of organic contamination of the surface, and several processing steps using advanced equipment. The deposition is performed at room temperature, requiring incubation times of 1 to 4 hours.

The roughness of an implant surface has been shown to affect cell proliferation and also the local production of growth factors by the cells around an implant. In vitro studies of human osteoblasts have shown that surfaces of increased microscale roughness resulted in a reduced number of cells, lower cell proliferation and increased matrix production, compared to smoother surfaces (Martin J Y et al, Proliferation, differentiation, and protein synthesis of human osteoblast-like cells (MG63) cultured on previously used titanium surfaces, Clin Oral Implants Res, March 7(1), 27-37, 1996). Yet other studies have shown that surface roughness enhances cell differentiation, while reducing cell proliferation (Kieswetter K, Schwartz Z, Hummed T W, Cochran D L, Simpson J, Dean D D, Boyan B D, "Surface roughness modulates the local production of growth factors and cytokines by osteoblast-like MG-63 cells", J Biomed Mater Res, September, 32(1), 55-63, 1996). Increased cell differentiation implies a potentially improved rate of bone formation.

Recently, the modulation of adhesive capabilities of cells have advanced from micro to nanopatterning techniques. It is believed that cell function may be regulated by nanostructural physical signals by stimulating integrin-mediated focal adhesion and intracellular signaling in anchorage-dependent cell function (Bershadsky A, Kozlov M, and Geiger B, "Adhesion-mediated mechanosensitivity: a time to experiment, and a time to theorize", Curr Opin Cell Biol, 18(5), 472-81, 2006).

EP 1440669B1 and related US 2004/0153154 A1 (Dinkelacker) disclose a bone implant having a surface which is reshaped to comprise a microstructure for anchoring the implant in the cell area. The microstructure, which is provided in the form of a cover layer applied on a previously roughened surface, comprises an array of densely packed rounded domes separated by rounded lacunae, the dimensions of the microstructure being approximately the same order of magnitude as the dimensions of the cells. The microstructural cover layer may be applied e.g. by sputtering. Further, a nanostructure, also obtained by sputtering, comprised of rounded domes separated by rounded lacunae is provided on the microstructure, wherein the dimensions of the nanostructure is approximately one decimal order of magnitude smaller than the corresponding dimensions of the microstructure. Again, however, there are potential problems with the stability of the cover layer and the integrity of the attachment between the cover layer and the implant body. Another technique for creating a desirable surface roughness is disclosed in EP 1 449 544 A1 (Wen et al) which provides a method for providing a metallic orthopaedic implant with a micrometre- or nanometre-scale surface roughness, while maintaining the structural integrity of the implant. In this method, an implant having metallic elements adhered to the implant surface, thus defining a porous surface geometry, is etched to produce a micrometre- or nanometre-scale surface roughness. For example, the metallic elements are metallic beads having a size from about 40 μm to several mm. However, this method is rather laborious and requires the use of advanced technical equipment, as the metallic elements are applied by a coating technique followed by sintering to fuse the elements to the implant surface and to each other. Consequently, the method is also expensive.

In brief, although there are today many existing techniques for improving the osseointegration of an implant, these methods generally suffer from drawbacks in respect of processability, cost-efficiency and biological effect and stability after implantation. Thus, there is a need in the art for improvement in the production of implants which have properties which even further promote osseointegration.

SUMMARY OF THE INVENTION

An object of the invention is to provide a biocompatible component having a desired rate of attachment between bone tissue and the component upon implantation thereof in bone tissue, and forming a mechanically strong bond with said bone tissue.

Another object of the invention is to provide a method for producing such a biocompatible component.

The passivating oxide normally covering titanium, zirconium, hafnium, tantalum, niobium and alloys thereof to a large extent provides the biocompatibility of these metals by preventing any chemical interaction between the metal and living tissue. However, by causing small defects in the oxide structure, the biocompatibility of metallic components may actually be further increased. The inventors have found that by treating a component having a metallic oxide surface by oxalic acid, a modified surface structure of the component is obtained, which has improved properties for implantation into living bone.

Thus, in one aspect, the present invention relates to a method for modification of a biocompatible component comprising the steps of
 a) providing a biocompatible component at least partly covered by metallic oxide; and
 b) treating at least a part of said component, which part is covered by said metallic oxide, with an aqueous composition comprising oxalic acid,
whereby a modified metallic oxide is obtained.

The component obtained by the inventive method has a hierarchical surface topography comprising a microstructure and a primary nanostructure superimposed on said microstructure, which has been found to increase the activity of bone-forming cells adhered thereto.

Esthetics becoming an increasingly important aspect of implantology, conventional titanium dental implants present an obstacle to a perfect esthetic solution, as the metallic grey lustre of a conventional titanium oxide surface may be visible through a patient's gingiva. Advantageously, the modified oxide surface obtained by the inventive method has a whitish colour, which is lighter and duller than the metallic grey colour of the surface of the component before treatment according to the invention. The whitish colour is very desirable for a dental component, as a natural-looking implant may be obtained. The whitish colour is best seen in a blasted component. The altered colour of the component may also be used as an indication that step b has been completed.

The concentration of oxalic acid in the composition of step b may be in the range of from 0.001 to 5 M, preferably about 1 M; and the treatment time of step b is in the range of from 10 to 60 minutes, preferably in the range of from 20 to 40 minutes, and more preferably about 30 minutes. The temperature of the composition of step b is typically in the range of from about 20° C. to about 100° C.; preferably in the range of from 60° C. to 90° C.; and more preferably about 80° C.

Optionally the above method further comprises the step of
c) treating at least part of said modified oxide with a second aqueous composition comprising
  i) at least one material selected from the group comprising ionised fluorine and ionised chlorine; and
  ii) at least one acid.

In particular, step c should be performed before a passivating oxide is formed on said modified metallic oxide. By performing step c before the modified oxide obtained in step b is covered by a passivating oxide, a surface having a uniformly distributed secondary nanostructure may be obtained, which promotes the osseointegration of the component. Thus, when the component is kept at a temperature above 0° C., e.g., room temperature, at normal atmospheric pressure and in an oxygen-containing atmosphere, the interval between step b and step c is preferably as short as possible to avoid the formation of passivating oxide on the surface of the component. Under such conditions, step c may be performed within 180 hours or less after the completion of step b, for example 72 hours, 36 hours, 24 hours or 1 hour after step b. Preferably, step c is performed within 30 minutes or less after the completion of step b, and more preferably within 10 or minutes less after the completion of step b.

The second aqueous composition may have a pH in the range of from 0.5 to 5, preferably from 1 to 3, and more preferably about 2; and the concentration of ionised fluorine and/or chlorine may be in the range of from about 0.05 to 0.5 M, preferably about 0.1 M. The active treatment time of step c is in the range of from 10 seconds to 60 minutes, preferably in the range of from 10 seconds to 3 minutes, and more preferably in the range of from 10 seconds to 50 seconds. The temperature of the composition of step c is typically in the range of from 15 to 25° C.; and preferably in the range of from 18 to 23° C.

The inventive method uses aqueous solutions only, thus avoiding problems related to organic solvents, such as organic residues remaining on the surface of the component. The aqueous solution which is used in step c preferably comprises hydrofluoric acid.

The method also uses simple equipment, is easily performed and is robust. Thus, the method according to the invention is cost-efficient and suitable for industrial applicability. Furthermore, the treatment time is advantageously short.

Further, the osseointegration of the component may be enhanced by including a bone-growth enhancing material in the surface of the component. This surface may for example be achieved by including metal ions or salt thereof, which metal ions may be selected from the group consisting of titanium ions, magnesium ions, calcium ions, lithium ions, strontium ions or any combination thereof, into the aqueous compositions of step b and/or step c. In particular, the inventors have found that lithium or strontium ions locally administered in bone tissue have a local effect on the bone formation and bone mass in said bone tissue. It has further been found that an implant comprising a surface oxide containing and/or releasing ionised lithium or strontium provides an improved rate of bone formation in comparison to an implant comprising a surface oxide layer containing, for instance, ionised calcium or magnesium. Thus, the composition of step b and/or the composition of step c may comprise lithium and/or strontium or a salt thereof. In order to provide a favourable substrate for osseointegration, the biocompatible component preferably at least partly consists of titanium or a titanium alloy. Accordingly, said metallic oxide preferably comprises titanium oxide. The metallic oxide may consist essentially of a titanium oxide or a combination of titanium oxides. The metallic oxide may be passivating titanium oxide.

In order to provide the component with a desirable initial surface roughness or desirable chemical characteristics, the biocompatible component may be subjected to a mechanical and/or chemical surface treatment prior to step b. A chemical treatment may for example comprise a cleaning process to remove undesired substances which may negatively affect the result of the method of the invention or the biocompatibility of the component. A roughening treatment, such as blasting, may further enhance the osseointegration of the component and improve the biomechanical properties thereof.

In another aspect, the invention relates to a component which is obtainable by a method as described above.

The inventors have found that a surface having a hierarchical surface topography comprising a microstructure and a primary nanostructure superimposed on said microstructure provides an implant surface which is improved in respect of osseointegration and biomechanical interaction with bone tissue. Thus, in another aspect, the invention relates to a biocompatible component, comprising a substrate having a surface comprising
a) a microstructure comprising micropits separated by plateus and/or ridges; and
b) a primary nanostructure being superimposed on said microstructure, said primary nanostructure comprising depressions arranged in wave-like formation.

The inventors have found that the above surface promotes osteoblast differentiation and secretion of bone precursor material. The microstructure provides an underlying microroughness comprising pore-like pits, resembling cell culture dishes, which stimulate cells to proliferate and differentiate. Possibly, the surface topography comprising the microstructure and the primary nanostructure resembles the topology of a site in living bone where bone resorption has occurred. It is believed that the surface topography of the component of the invention fits the expectations of pre-osteoblast cells present around an implant site, and by mimicking the surface of natural bone prepared by osteoclasts for bone remodeling, osteoblast activity may be quickly and strongly induced by a component according to the invention. The microstructure may have a pit diameter in the range of from 0.5 to 15 μm, and preferably from 1 to 10 μm; and a depth in the range of from 0.1 to 2.5 μm, and preferably from 0.1 to 1 μm. The distance between adjacent micropits may be up to 10 μm. The depressions of the primary nanostructure have a diameter in the range of from 10 nm to 1 μm, preferably in the range of from 10 nm to 600 nm, and more preferably in the range of from 10 nm to 500 nm. The depth may be in the range of from 10 nm to 300 nm, and is typically in the range of from 30 to 150 nm.

Furthermore, the diameter of an individual depression of the primary nanostructure typically exceeds the depth of the same depression.

As mentioned above, the primary nanostructure is superimposed on the primary microstructure. Furthermore, the diameter and depth, respectively, of a primary nanostructure each is smaller than the corresponding dimension of an individual pit of the microstructure. Thus, an individual pit of the microstructure typically comprises multiple depressions of the primary nanostructure. Furthermore, a boundary of a depression of the primary nanostructure typically constitutes a boundary of another depression of the primary nanostructure.

Furthermore, the above described surface may further comprise a secondary nanostructure comprising discrete nanoelements being superimposed on said primary nanostructure in a uniformly distributed pattern and having the shape of rounded projections. The secondary nanoelements, it is believed, improve the anchoring of the cells to the underlying surface and further stimulate cell activity.

The secondary nanostructure of the biocompatible component of the invention may have a peak diameter in the range of from 20 to 550 nm, preferably from 20 to 150 nm; and an average peak height of from 5 to 200 nm, preferably from 5 to 100 nm. The peak-to-peak distance is typically in the range of from 10 to 450 nm, and preferably from 40 to 200 nm. The peak density is typically in the range of from 15 to 150 peaks/$\mu m^2$, and preferably from 50 to 130 peaks/$\mu m^2$.

At a bone tissue-bone implant interface, a tissue layer generally forms which contains a reduced amount of collagen and minerals, and thus has a decreased strength compared to normal, healthy bone. The thickness of this tissue layer determines the mechanical strength of the bone-implant interface (Albrektsson, T et al, "Ultrastructural analysis of the interface zone of titanium and gold implants", Advances in Biomaterials 4, 167-177, 1982; Albrektsson, T et al, "Interface analysis of titanium and zirconium bone implants", Biomaterials 6, 97-101, 1985; Albrektsson T, Hansson, H-A, "An ultrastructural characterization of the interface between bone and sputtered titanium or stainless steel surfaces", Biomaterials 7, 201-205, 1986; Hansson, H-A et al, "Structural aspects of the interface between tissue and titanium implants", Journal of Prosthetic Dentistry 50, 108-113, 1983; Johansson, C et al, "Ultrastructural differences of the interface zone between bone and Ti6A14V or commercially pure titanium", Journal of Biomedical Engineering 11, 3-8, 1989; Johansson, C. et al, "Qualitative, interfacial study between bone and tantalum, niobium or commercially pure titanium", Biomaterials 11, 277-280, 1990; Sennerby, L et al, "Structure of the bone-titanium interface in retrieved clinical oral implants", Clinical Oral Implants Research 2, 103-111, 1991; Sennerby, L et al, "Ultrastructure of the bone-titanium interface in rabbits", Journal of Materials Science: Material in Medicine 3, 262-271, 1992; Sennerby, L et al, "Early tissue response to titanium implants inserted in rabbit cortical bone, Part II: Ultrastructural observations", Journal of Materials Science: Material in Medicine 4, 494-502, 1993) The hierarchical surface topography comprising the microstructure and the primary nanostructure provides an improved mechanical interaction between the component and the subsequently formed bone tissue, which is believed to result in the formation of a less thick tissue layer of reduced strength. The secondary nanostructure further improves the mechanical interaction between the biocompatible component and the surrounding bone tissue after implantation. Hence, the biocompatible component of the invention provides a bone tissue-implant interface of improved shear and tensile strength.

Furthermore, in order to provide the component with a desired initial surface roughness or desired chemical characteristics, the substrate may be subjected to a mechanical and/or chemical surface treatment. A chemical treatment may for example comprise a cleaning process. A roughening treatment, such as blasting, may provide a surface structure in which the diameters and depths of the subsequently formed microstructure and the diameters of the primary nanostructure are less variable (i.e, having smaller standard deviation values). The increased homogeneousness of the surface of the component of the invention may further enhance the osseointegration of the component and improve the biomechanical properties thereof.

The biocompatible component substrate typically at least partly consists of titanium or a titanium alloy. Preferably, the substrate consists of titanium. Furthermore, the secondary nanostructure may comprise metallic oxide, preferably titanium oxide. The homogeneousness of the component surface, which may consist of metallic oxide only, is very advantageous in respect of the long-term stability and integrity of the component after implantation. Additionally, the component surface structure is stable with respect to sterilisation procedures and shelf storage.

The osseointegration of the component of the invention may be further enhanced by comprising a bone-growth enhancing material, in the surface of the component. Such a surface may for example be achieved by including metal ions, for example those selected from the group consisting of titanium ions, magnesium ions, calcium ions, lithium ions, strontium ions or any combination thereof in the surface. In particular, the inventors have found that lithium or strontium ions locally administered in bone tissue may have a local effect on the bone formation and bone mass in said bone tissue. Thus, the surface of the component of the invention may comprise lithium and/or strontium or a salt thereof.

The biocompatible component of the invention may be a dental component, for example an implant, a fixture, an abutment, or combinations thereof, such as a one-piece implant. The biocompatible component may also be an orthopaedic component, such as a hip joint component intended for implantation into the neck of the femur of a patient.

In another aspect, the invention relates to a method for implanting a biocompatible component into the human or animal body comprising the steps of
   i) providing a biocompatible component according to the above description; and
   ii) implanting said biocompatible component into the body of a human or an animal.
For example, the component may be implanted into a periodontal area of the body of a human or an animal.

DETAILED DESCRIPTION OF THE INVENTION

Figure 1:
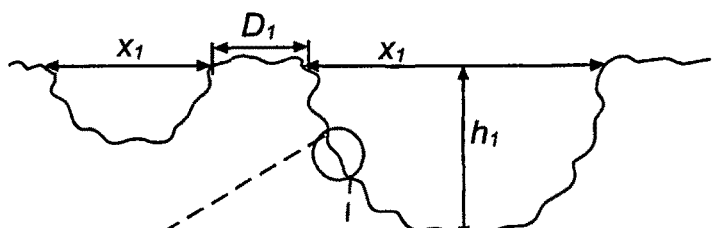
FIG. 1 is a schematic illustration defining the parameters used in respect of the microstructure.

As used herein, the term "biocompatible component" includes within its scope any component which is intended for long-term or short-term contact with living tissue and which, upon said contact, does not evoke significant adverse biological reaction of the tissue. One example of a biocompatible component is an implant, such as a dental implant.

As used herein the term "implant" includes within its scope any device of which at least a part is intended to be implanted into the body of a vertebrate animal, in particular a mammal, such as a human. Implants may be used to replace anatomy and/or restore any function of the body.

Generally, an implant is composed of one or several implant parts. For instance, a dental implant usually comprises a dental fixture coupled to secondary implant parts, such as an abutment and/or a restoration tooth. However, any device, such as a dental fixture, intended for implantation may alone be referred to as an implant even if other parts are to be connected thereto.

As used herein, the term "passivating (metallic) oxide" refers to naturally formed oxide, also referred to as native oxide, which is stable, does not grow substantially thicker over time and which prevents any substantial chemical reaction of the underlying substrate with an external agent. Passivating titanium oxide formed on titanium in contact with atmospheric oxygen generally has a thickness of 2-5 nm.

As used herein, the term "bone-growth enhancing material" includes within its scope any substance which is capable of promoting bone formation, (e.g., promoting adhesion, proliferation and differentiation of osteoblasts or pre-osteoblasts; promoting the production of bone matrix components, secretion of bone matrix components, mineralisation of bone matrix; and inhibition of osteoclast activity), either alone or in combination with other substances.

As used herein, the term "microstructure" refers to a physical structure of dimensions generally ranging from 0.5 μm to 100 and the term "nanostructure" refers to a physical structure of dimensions generally ranging from 0.1 nm to 500 nm.

The biocompatible component of the invention may be a dental component, for example an implant, a fixture, an abutment, or combinations thereof, such as a one-piece implant. The biocompatible component may also be an orthopaedic component, such as a hip joint component intended for implantation into the neck of the femur of a patient.

The biocompatible component of the invention may consist of any suitable material, such as a metal, e.g. titanium or an alloy thereof, zirconium or an alloy thereof, hafnium or an alloy thereof, niobium or an alloy thereof, tantalum or an alloy thereof, a chromium-vanadium alloy or any combination of these materials, or a non-metal. The biocompatible component may be provided with a metallic layer, for example an applied metallic surface layer covering a non-metallic body or a body partly consisting of a non-metallic material. Examples of non-metallic materials comprise a ceramic, a plastic and a composite material.

The metallic oxide may be a naturally air-formed oxide, or it may be formed in any kind of treatment prior to the method according to the invention.

The biocompatible component may be subjected to any kind of pretreatment in order to create a desired substrate surface for further modification according to the inventive method. For example, the component may be pretreated by a mechanical, chemical or thermal treatment, or any combination thereof, to obtain a desired initial surface composition or roughness. A mechanical treatment may for instance comprise a blasting process. A chemical treatment may for instance comprise a cleaning or degreasing process. in one aspect, the present invention relates to a method for modification of a biocompatible component.

According to the inventive method, at least a part of the biocompatible component is subjected to treatment with an aqueous composition comprising oxalic acid, whereby a modified metallic oxide is obtained (referred to as "step b"). In this treatment, the modified metallic oxide is dissolved and the underlying substrate is etched while new oxide is formed on the biocompatible component. The oxide dissolution and reoxidation processes occur simultaneously.

The part of the biocompatible component to be treated is at least partly covered by said metallic oxide. In embodiments of the invention, step b is performed by placing the component in an aqueous solution of oxalic acid at an elevated temperature under vigorous agitation for a period of time. Alternatively, only part of the component may be immersed in the composition, e.g. by dipping. A part of the component not intended to be treated may be masked during the treatment.

The pH of the composition of step b should be acidic, such as pH 5 or below, pH 2 or below, or pH 0.7 or below. Preferably, the pH is as low as possible in view of processing convenience.

The aqueous composition comprising oxalic acid may be an aqueous solution comprising oxalic acid at a concentration in the range of from about 0.001 to about 5 M, e.g., a solution of oxalic acid at a concentration within said range. Preferably, the concentration of oxalic acid in the composition is in the range of 0.01 to 2 M, more preferably in the range of from 0.1 to 2 M and most preferably about 1 M.

For the purpose of step b, at least a part of the biocompatible component may be immersed in the composition comprising oxalic acid for a period of time in the range of from about 5 to about 60 minutes, for example from 20 to 40 minutes. Typically, the duration of the treatment of step b is about 25 minutes or about 30 minutes. The treatment of step b is considered to be completed at the moment when the component is removed from the aqueous composition comprising oxalic acid.

The temperature of the aqueous composition may be in the range of from about 20° C. to about 100° C. Typically, the temperature of the aqueous composition comprising oxalic acid may be in the range of from 60° C. to 90° C., for example about 80° C.

As an example, the treatment of step b may be performed using an concentration of oxalic acid of about 1 M at a temperature of 80° C. for 30 minutes.

When a titanium component is used, the modified oxide obtained in step b is more reactive than passivating titanium oxide formed in air, and it has a higher water content than passivating titanium oxide formed in air. Possibly, the modified titanium oxide of the invention is more amorphous than passivating titanium oxide formed in air or formed in a chemical cleaning pretreatment. The surface structure of the modified oxide obtained in step b comprises a microstructure and a primary nanostructure of which examples are shown in FIGS. 5 and 6, and which will be described in more detail below.

The surface of the biocompatible component obtained in step b has a colour which is lighter and duller than the metallic grey colour of the surface of the component before treatment according to the method of the invention. However, there is a difference in colour between a component according to the invention which was pretreated by blasting, and a component according to the invention which was simply machine worked, the blasted component having a whiter colour than the machine worked component. The altered colour may be used as an indication that step b has been completed. However, the altered colour is more clearly seen after 2 minutes of washing in an ultrasonic bath.

Following step b, at least a part of the modified oxide may be subjected to treatment with a second aqueous composition comprising at least one material selected from the group consisting of ionised fluorine and ionised chlorine, and at least one acid (referred to as "step c"). By step c, part of the modified metallic oxide formed in step b dissolves and subsequently precipitates to form a secondary nanostructure comprising uniformly distributed rounded projections of metallic oxide which are superimposed on said microstructure and primary nanostructure. Alternatively, any other compound which forms a complex with the metal of the dissolving metallic oxide may be used. Fluorine and chlorine are known titanium complexing agents.

When the component is kept at a temperature of at least 0° C. at normal atmospheric pressure and in an oxygen-containing atmosphere such as air, step c should be performed within a relatively short period of time after the completion of step b. Step b is considered to be completed as soon as the component is removed from the aqueous composition of step b. More particularly, step c should be performed before the modified metallic oxide obtained in step b is covered by passivating oxide formed thereon. The passivating oxide is considered to be formed when it prevents any substantial chemical reaction of the underlying material with an external agent. The reactivity of the modified oxide obtained in step b is vital to achieving a uniform distribution of the rounded peaks of the secondary nanostructure. It is believed that during the step c treatment, the acid attacks the modified oxide at a multitude of active sites to dissolve the oxide. Hydrogen gas generated in this process increases the pH locally at each active site. The locally elevated pH causes metallic oxide to precipitate at the active site, provided that the aqueous composition has a sufficiently high concentration of metallic material. Dissolution of modified titanium oxide obtained in step b may provide a sufficiently high titanium concentration for the titanium oxide to precipitate. As a passivating oxide forms gradually over time in the presence of oxygen, a shorter time interval between step b and step c will improve the final result of step c when the component is kept at a temperature of at least 0° C., e.g, room temperature (15 to 25° C.), at normal atmospheric pressure and in an oxygen-containing atmosphere. Thus, under such conditions, the interval between step b and step c is preferably kept as short as possible. Step c may be performed up to within 180 hours after the completion of step b, for example 72 hours, 36 hours, 24 hours or 1 hour after step b. Preferably, step c is performed within 30 minutes or less after the completion of step b, more preferably within 10 minutes or less, and most preferably within 3 minutes or less after the completion of step b. However, if the component is kept in an inert atmosphere or otherwise prevented from forming a passivating oxide surface, the time interval between step b and step c may be considerably longer. To avoid the formation of a passivating oxide, any atmosphere having a reduced amount of reactive oxygen, compared to normal air, may be used. For example, following step b, the component may be placed in an inert gas such as nitrogen, helium, neon, argon, krypton, xenon or radon. Alternatively, the component may be placed in an atmosphere of reduced pressure or in vacuum. Alternatively, the component may be cooled or frozen. Any combination of the above strategies for partly or completely inhibiting the formation of a passivating oxide may also be used. For example, the component may be subjected to step b and subsequently frozen or placed in an inert gas for an extended period of time, and then restored to normal conditions (a temperature of at least 0° C. at normal atmospheric pressure) in an oxygen-containing atmosphere. In such cases, the time between step b and step c spent by the component under said normal conditions in an oxygen-containing atmosphere should be 180 hours or less, for example 72 hours or less, 36 hours or less, 24 hours or less, 1 hour or less, 30 minutes or less, 10 minutes or less, or 3 minutes or less.

In embodiments of the invention, step c is performed by immersing the component in an aqueous solution of hydrofluoric acid. Alternatively, only part of the component may be immersed in the composition, e.g. by dipping. A part of the component not intended to be treated may be masked during the treatment.

The aqueous composition comprises at least one material selected from the group consisting of ionised fluorine and ionised chlorine, and at least one acid. The aqueous composition may be an aqueous solution having a pH in the range of from 0.5 to 5, preferably from 1 to 3 M, and more preferably about 2. The concentration of ionised fluorine and/or chlorine may be in the range of from about 0.05 to 0.5 M. For example, the composition may be a solution of hydrofluoric acid (HF) having a concentration within said range. Preferably, a concentration of hydrofluoric acid in the range of from about 0.1 to 0.3 M, and more preferably about 0.1 M, is used.

The step c treatment is considered to be starting when the acid may be observed to act on the substrate surface. This activity may be detected by the formation of hydrogen gas at the component surface, which usually takes place after about 20-30 seconds at room temperature. Thus, by the term "active treatment" is meant treatment which is performed starting with the formation of the first bubble of hydrogen gas. The active treatment time of step c is in the range of from 10 seconds to 60 minutes; such as from seconds to 3 minutes, from 10 seconds to 2 minutes, from 10 to 60 seconds, from 10 to 50 seconds, from 10 to 40 seconds, and from 10 to 30 seconds.

Step c may be performed at ambient temperature. Typically, the aqueous composition of step c may have a temperature in the range of from to 25° C., e.g. a temperature in the range of from 18 to 23° C.

As an example, the treatment of step c may be performed using hydrofluoric acid at a concentration of about 0.1 M at room temperature for an active treatment time of 40 seconds.

It will be appreciated that the adjustment of any one of the parameters treatment time, temperature, pH and concentration may require appropriate adjustment of any other one of said pararametres within the above-mentioned ranges in order to obtain an acceptable result.

Figure 8:
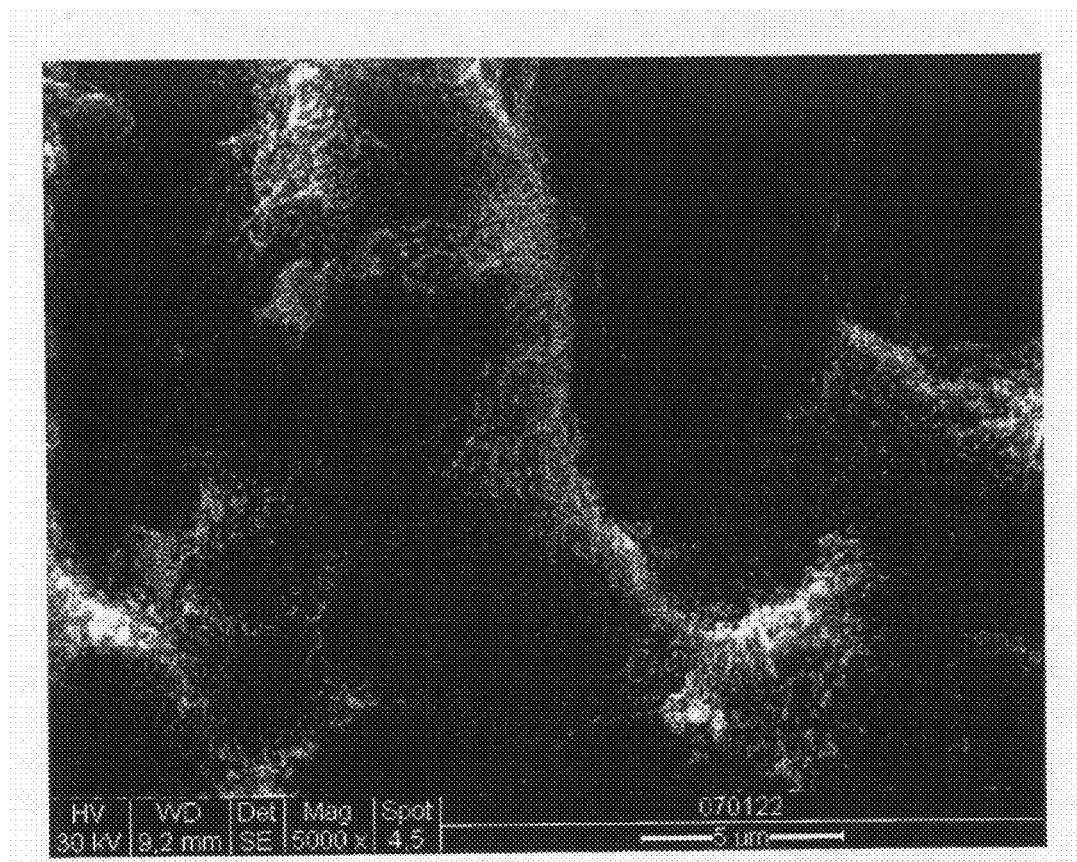
FIG. 8 is a scanning electron microscopy image of a blasted titanium sample according to the invention.
Figure 9:
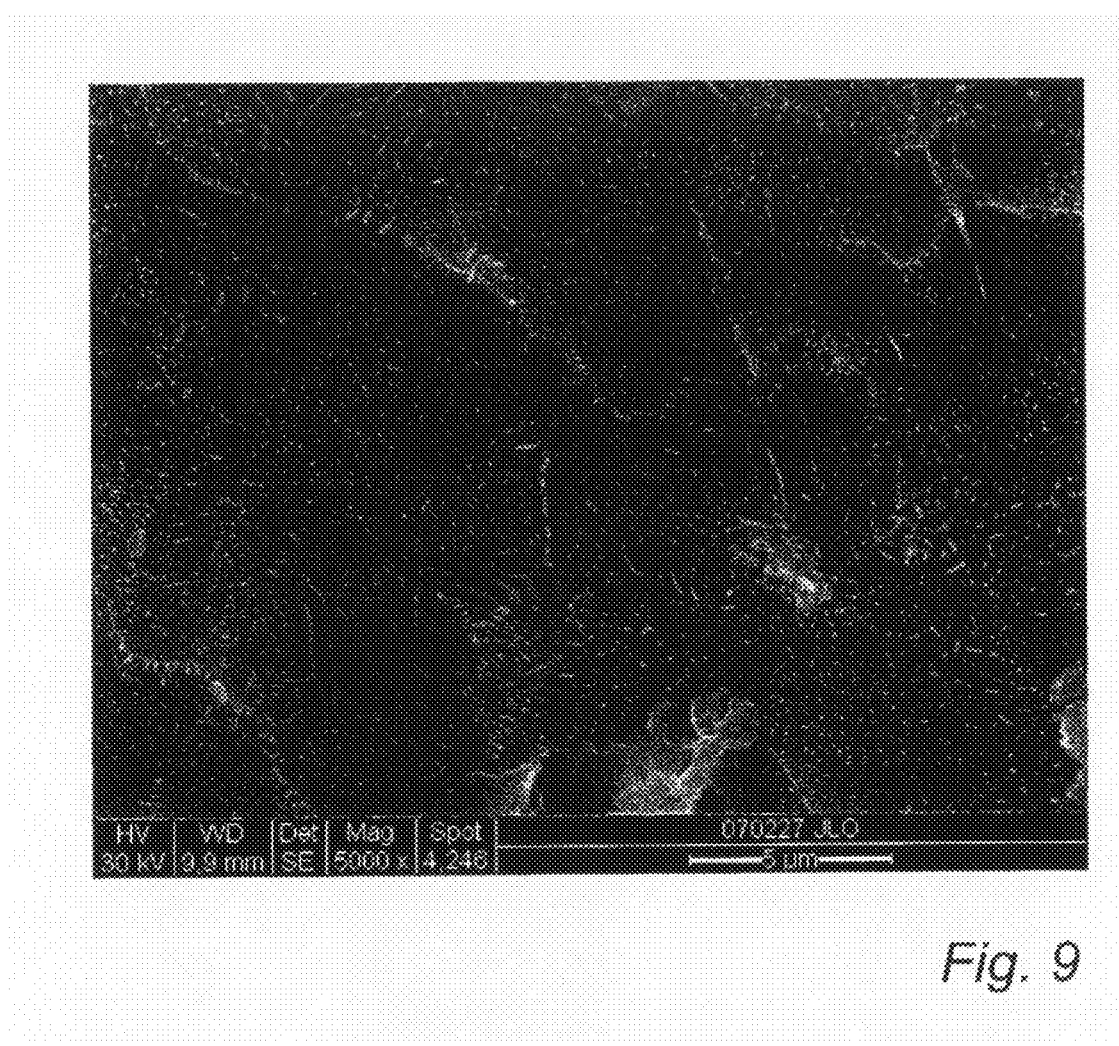
FIG. 9 is a scanning electron microscopy image of a titanium sample according to the invention.

By step c, the hierarchical surface structure obtained in step b is generally maintained, although its finer structures may be partly dissolved. The surface structure obtained after step c is shown in FIGS. 8 and 9 and will be described in more detail below. In embodiments of the invention, metallic oxide originating from the dissolution of modified metallic oxide obtained in step b precipitates to form a secondary nanostructure comprising uniformly distributed rounded peaks on top of the microstructure and the primary nanostructure. In embodiments of the invention, the peaks of the secondary nanostructure thus consist of metallic oxide. Soluble metal compounds may also be separately added to the aqueous composition of step c in order to increase the metal concentration of the step c composition.

Optionally, the compositions used in step b and step c may comprise a bone-growth enhancing material. The bone-growth enhancing material may comprise metal ions, such as titanium ions, magnesium ions, calcium ions, lithium ions and/or strontium ions, or a salt thereof. These ions may be separately added to the composition. For example, either the composition of step b or the composition of step c may comprise any of the above metal ions. Alternatively, both compositions may comprise metal ions. When both compositions comprise metal ions, they may comprise the same species or different species of metal ions. By incorporation of the above metal ions or any combination thereof, a modified surface may be obtained comprising said ions and/or salt(s) thereof, which has altered chemical properties. Thus the biocompatibility of the component may be improved and the osseointegration of the component may be stimulated.

In particular, the inventors have found that lithium or strontium ions locally administered in bone tissue has a local effect on the bone formation and bone mass in said bone tissue. It has further been found that an implant comprising a surface containing and/or releasing ionised lithium or strontium provides an improved rate of bone formation, and thus an improved rate of attachment between bone tissue and the implant in comparison to an implant comprising a surface oxide containing, for instance, ionised calcium or magnesium. Thus, in embodiments of the invention, both the compositions of step b and step c, or the composition of step b only, comprise(s) ionised lithium or strontium or a combination thereof. Alternatively, only the composition of step c comprises ionised lithium or strontium or a combination thereof.

Alternatively, a bone-growth enhancing material, such as ionised lithium or strontium, may be applied on the surface of the component after the performance of step b or step c according to the invention.

In another aspect, the invention relates to a biocompatible component obtainable by the method described above, and to a method for implanting the biocompatible component into the body of a human or an animal. For example, the biocompatible component may be implanted into a periodontal area of the body of a human or an animal.

In another aspect, the invention relates to a biocompatible component having a hierarchical surface structure comprising a microstructure, a primary nanostructure superimposed on said microstructure and optionally a secondary nanostructure superimposed on said primary nanostructure.

Figure 2:
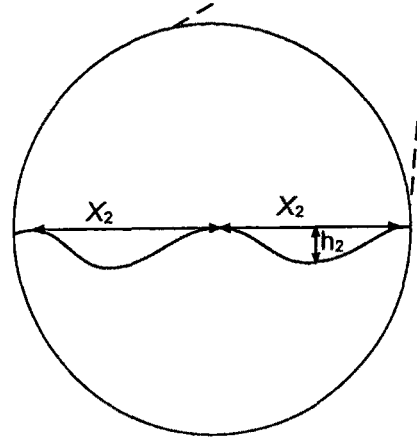
FIG. 2 is a schematic illustration defining the parameters used in respect of the primary nanostructure.

The terms "depth" ($h_1$), "diameter" ($x_1$) and "distance" ($D_1$) in respect of a profile of the microstructure are defined in FIG. 1. The depth ($h_1$) of a pit is defined as the distance between an imaginary line drawn between two adjacent peaks and the intermediate surface at its lowest point. If no well-defined peaks are present, the imaginary line is drawn between those points where the surface profile starts to deviate from an essentially flat surface profile (a plateau). The diameter ($x_1$) of a pit and the distance ($D_1$) between adjacent pits are the distances between said adjacent points as defined in FIG. 1. In FIG. 1, a superimposed primary nanostructure is also schematically provided on the microstructure. The terms "depth" ($h_2$) and "diameter" ($x_2$) in respect of the primary nanostructure are correspondingly defined in FIG. 2.

Figure 3:
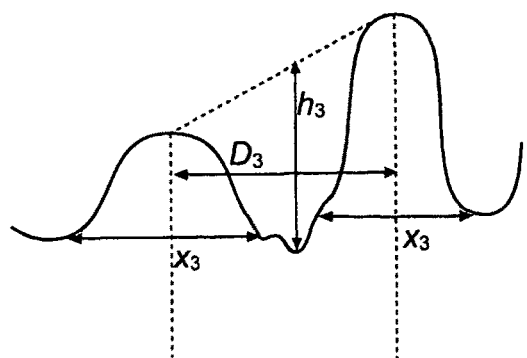
FIG. 3 is a schematic illustration defining the parameters used in respect of the secondary nanostructure.

The terms "height" ($h_3$), "diameter" ($x_3$) and "peak-to-peak distance" in respect of the secondary nanostructure are defined in FIG. 3. The peak height is defined as the distance between an imaginary line drawn between two adjacent peaks and the intermediate surface at its lowest point. The peak diameter ($x_3$) is measured between those points of the peak where the surface profile starts to deviate from an essentially flat surface profile.

Figure 4:
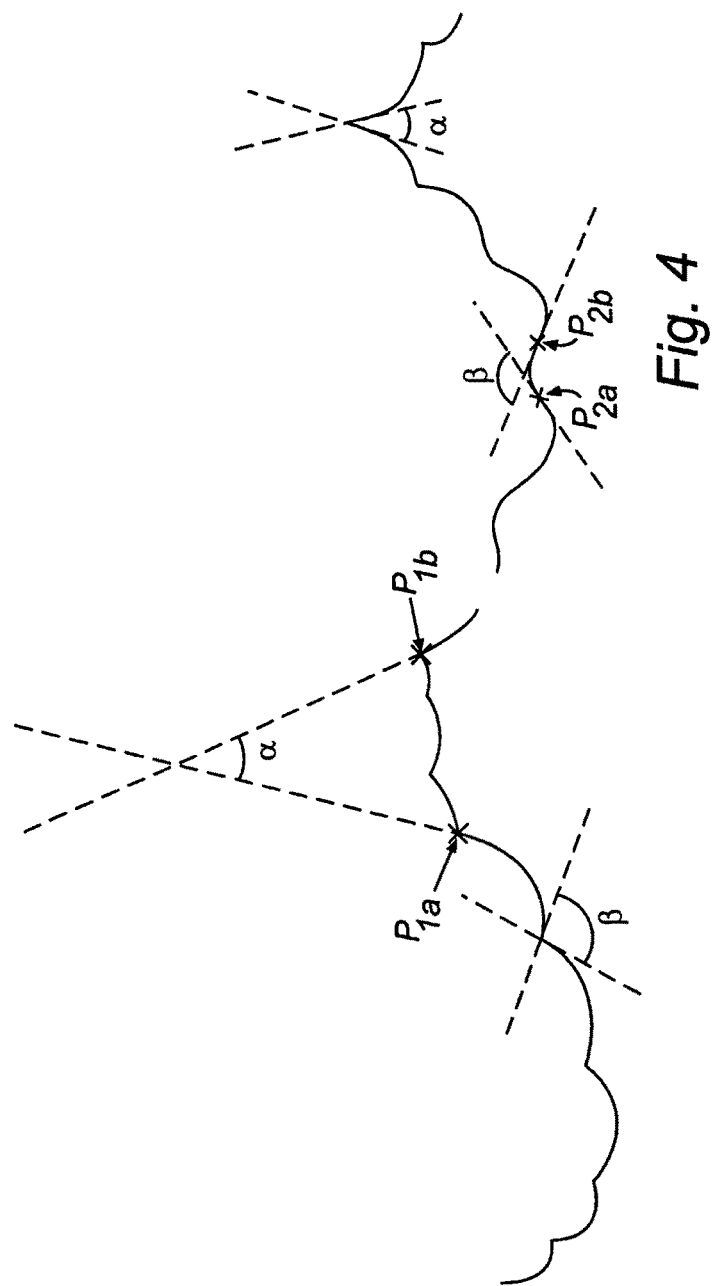
FIG. 4 is a schematic illustration defining the angles used in respect of the microstructure and the primary nanostructure, respectively.

In FIG. 4, the angle $\alpha$ in respect of a profile of the microstructure and the angle $\beta$ in respect of a profile of the primary nanostructure are defined. The angle $\alpha$ is defined as the angle between two imaginary lines, one of which representing the slope of a wall of a pit of the microstructure at the point where the surface profile starts to deviate from an essentially flat surface profile ($P_{1a}$), and one of which representing the slope of an adjacent wall of an adjacent pit of the microstructure at the point where the surface profile starts to deviate from an essentially flat surface profile ($P_{1b}$). Said mutually adjacent pits may thus be separated by a plateau. Accordingly, in the case where two adjacent pits are separated by a peak, the imaginary lines represent the inclinations of the walls at said peak. The angle $\beta$ is defined as the angle between two imaginary lines representing the slope of a wall of a depression of the primary nanostructure at its inflection point ($P_{2a}$) and the slope of an adjacent wall of an adjacent depression of the primary nanostructure at its inflection point ($P_{2b}$), respectively. In the case where two concave depressions are separated by a peak, the inflection point is thus located at said peak.

Figure 5A:
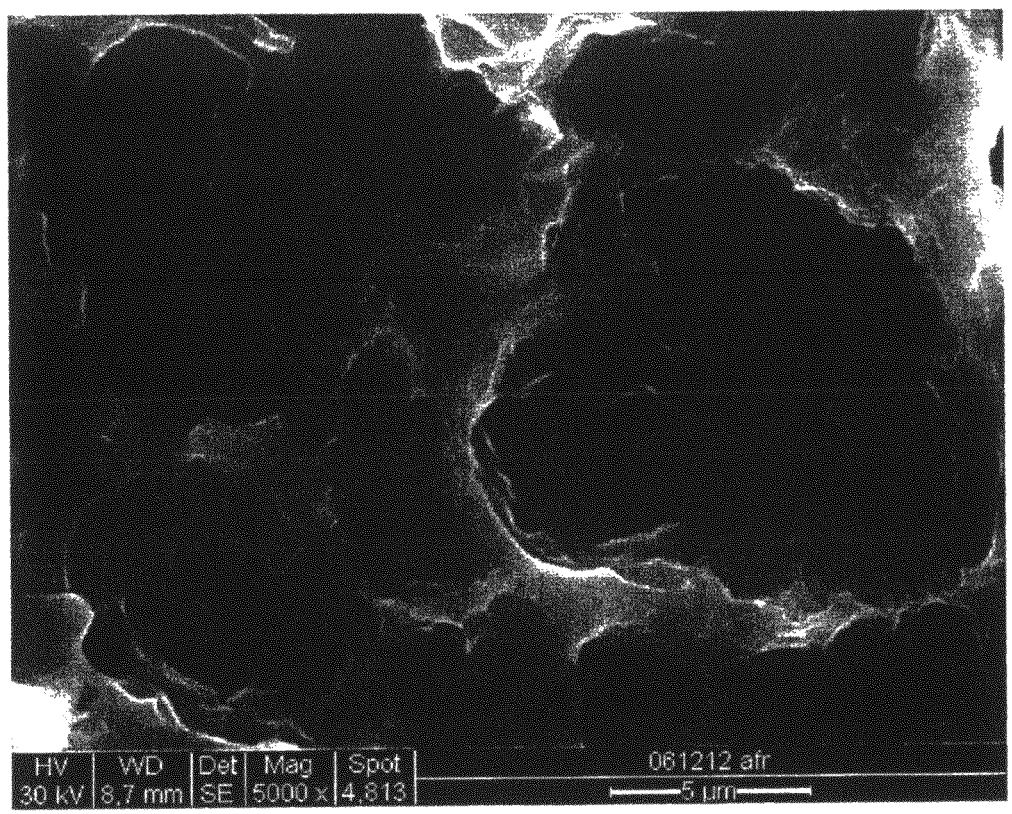
FIG. 5a is a scanning electron microscopy image of a titanium sample according to the invention.
Figure 5B:
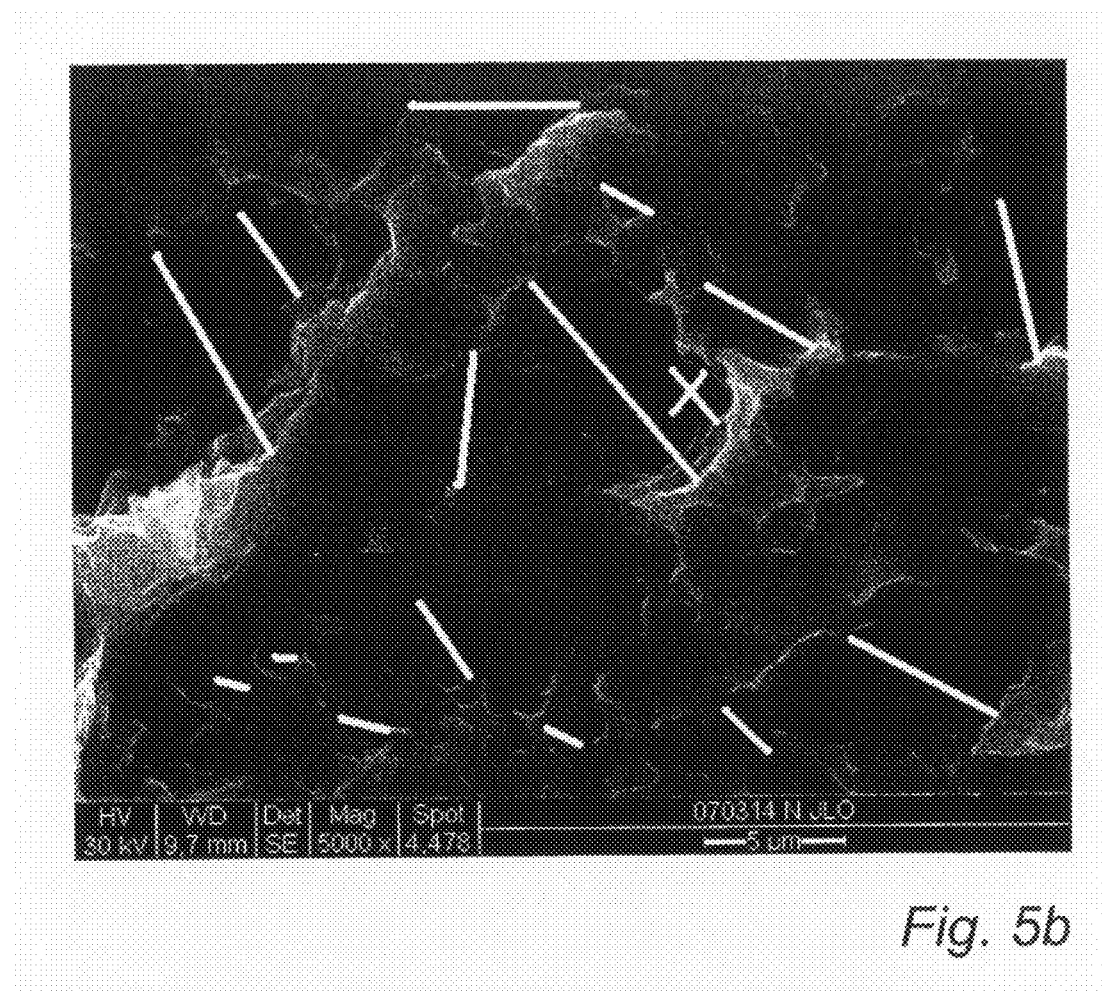
FIG. 5b is a scanning electron microscopy image of a titanium sample according to the invention, wherein diameters of the microstructure are marked.
Figure 6A:
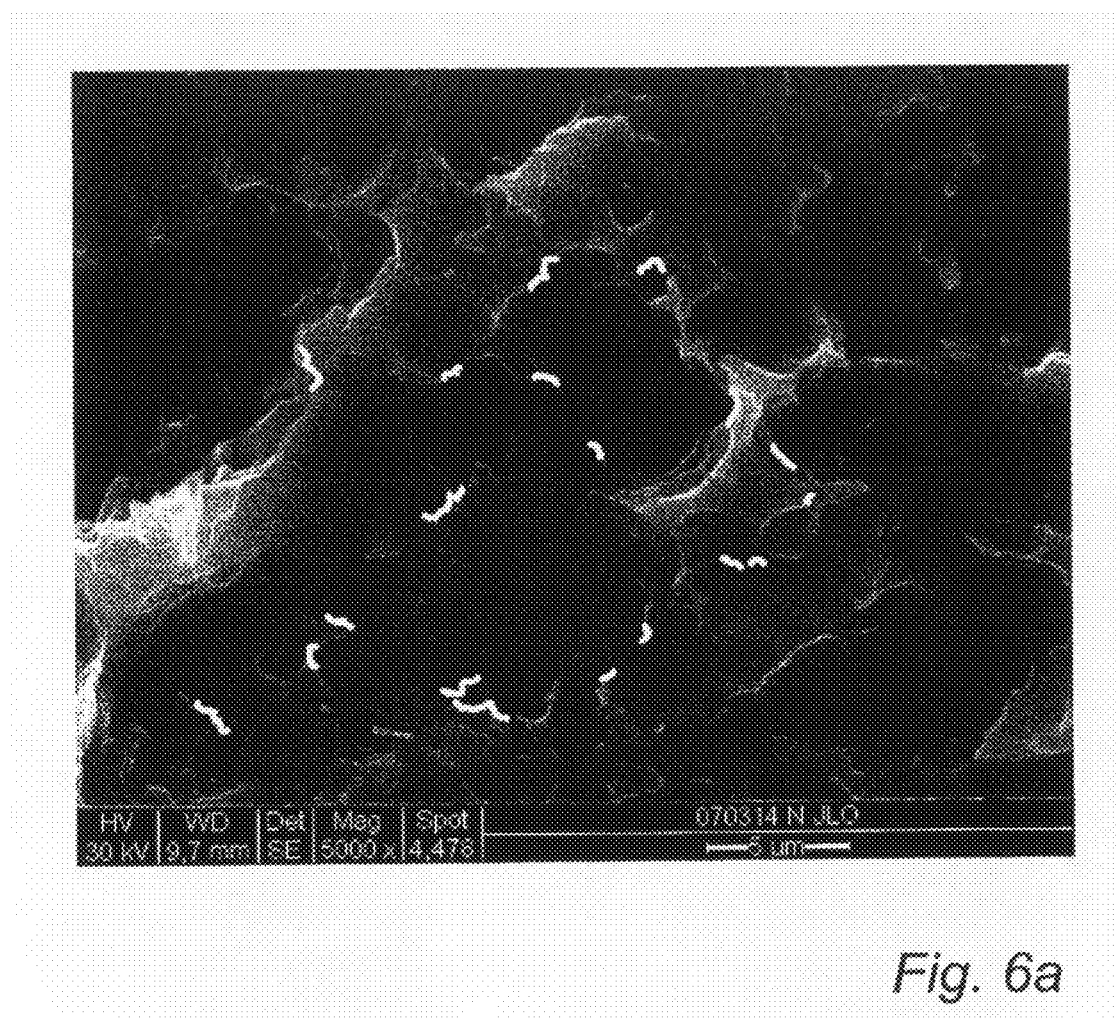
FIG. 6a is a scanning electron microscopy image of a titanium sample according to the invention, wherein depressions of the primary nanostructure are marked.
Figure 6B:
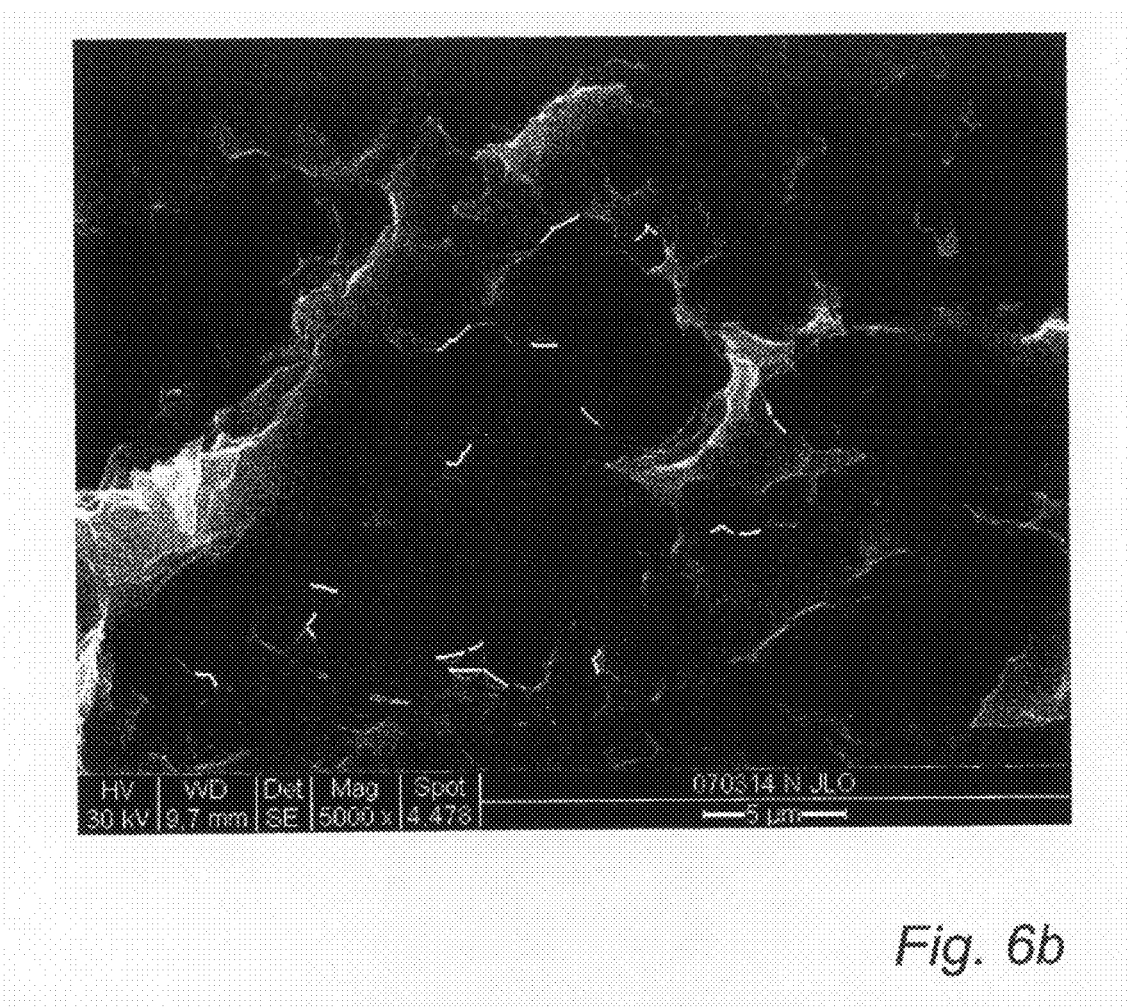
FIG. 6b is a scanning electron microscopy image of a titanium sample according to the invention, wherein diameters of the primary nanostructure are marked.

The microstructure and the primary nanostructure of the inventive component are essentially obtained in step b of the method described above. As described above, step b provides a modified oxide surface which is thickened, reactive, and has a white or whitish colour. FIG. 5a is a SEM image of a component after step b of the method of the invention showing said microstructure and said primary nanostructure. The component was pretreated by blasting. As is seen in this image, the microstructure comprises pore-like depressions or pits of different sizes. FIG. 5b is a SEM image of a component after step b according to the invention in which the diameters of some of the pits of the microstructure have been marked.

Figure 13A:
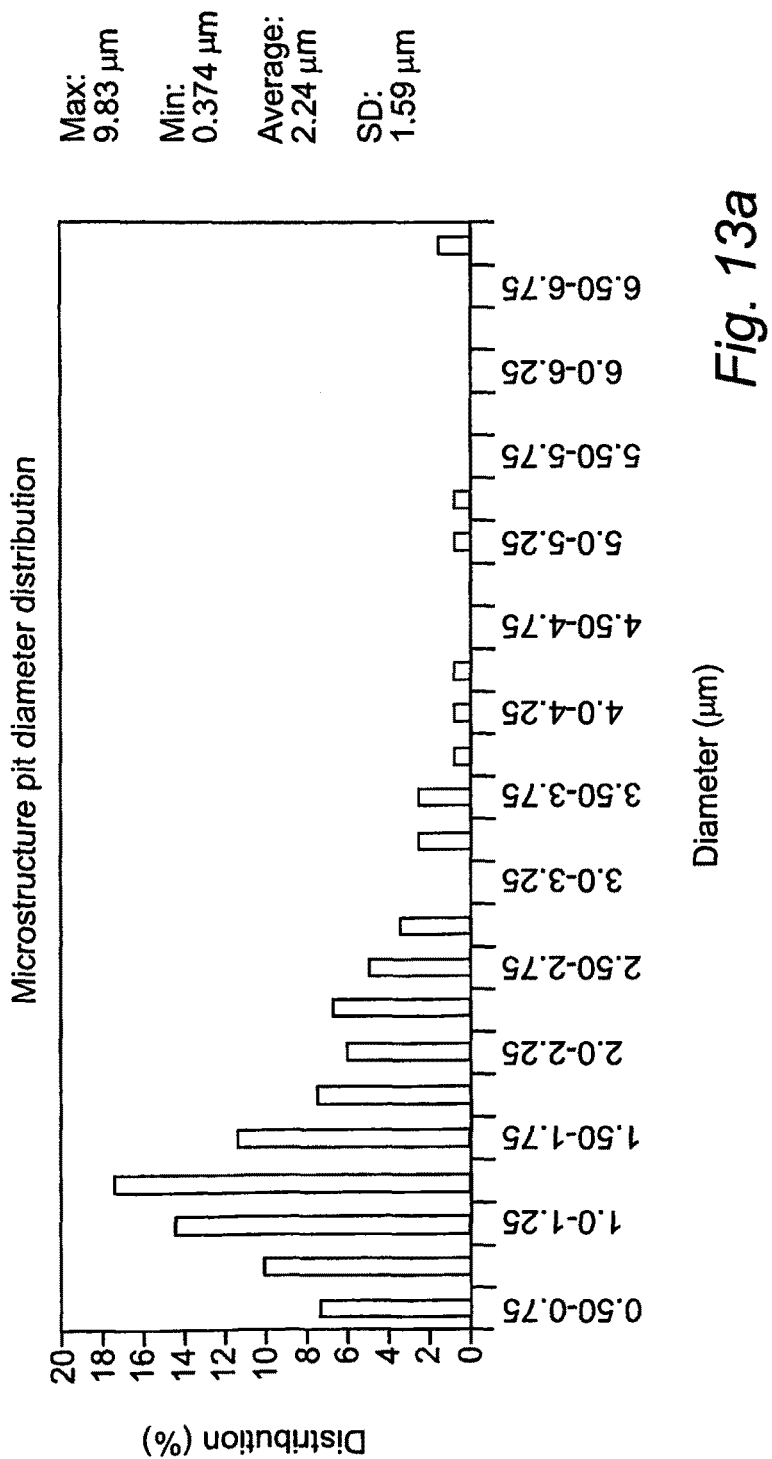
FIG. 13a-c are graphs showing the distribution of microstructure pit diameter, depth and distance between adjacent pits, respectively, in a titanium sample according to the invention.
Figure 13B:
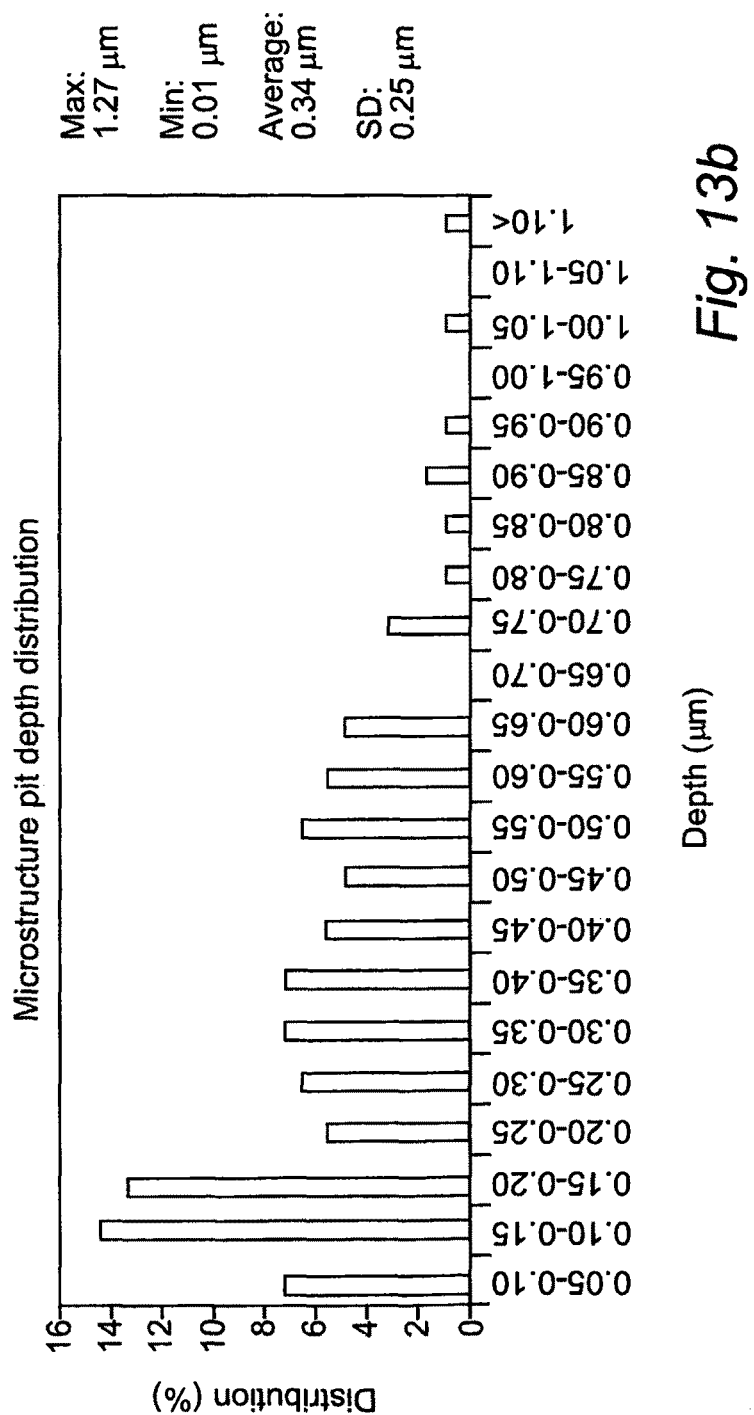
Figure 13C:
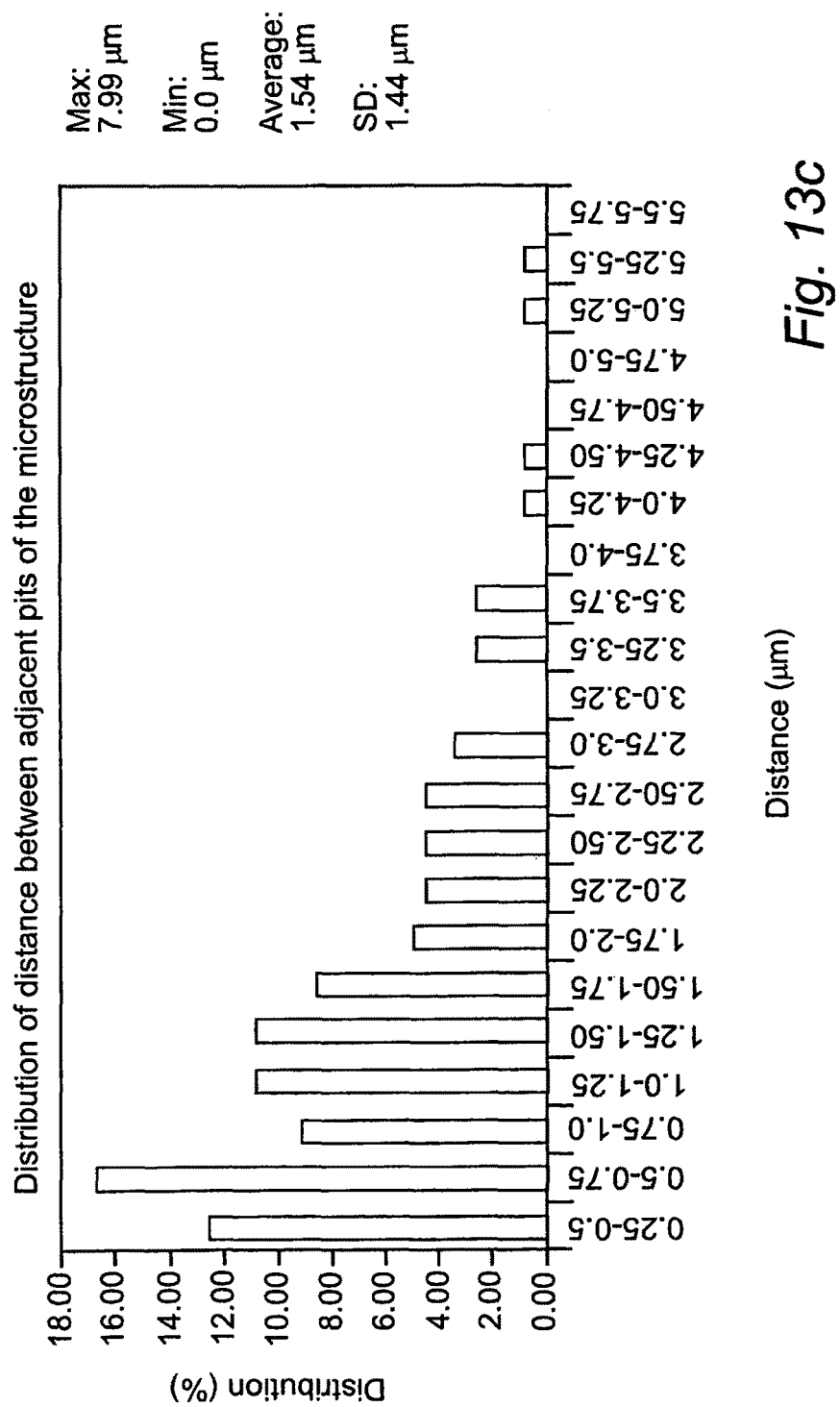
Figure 14A:
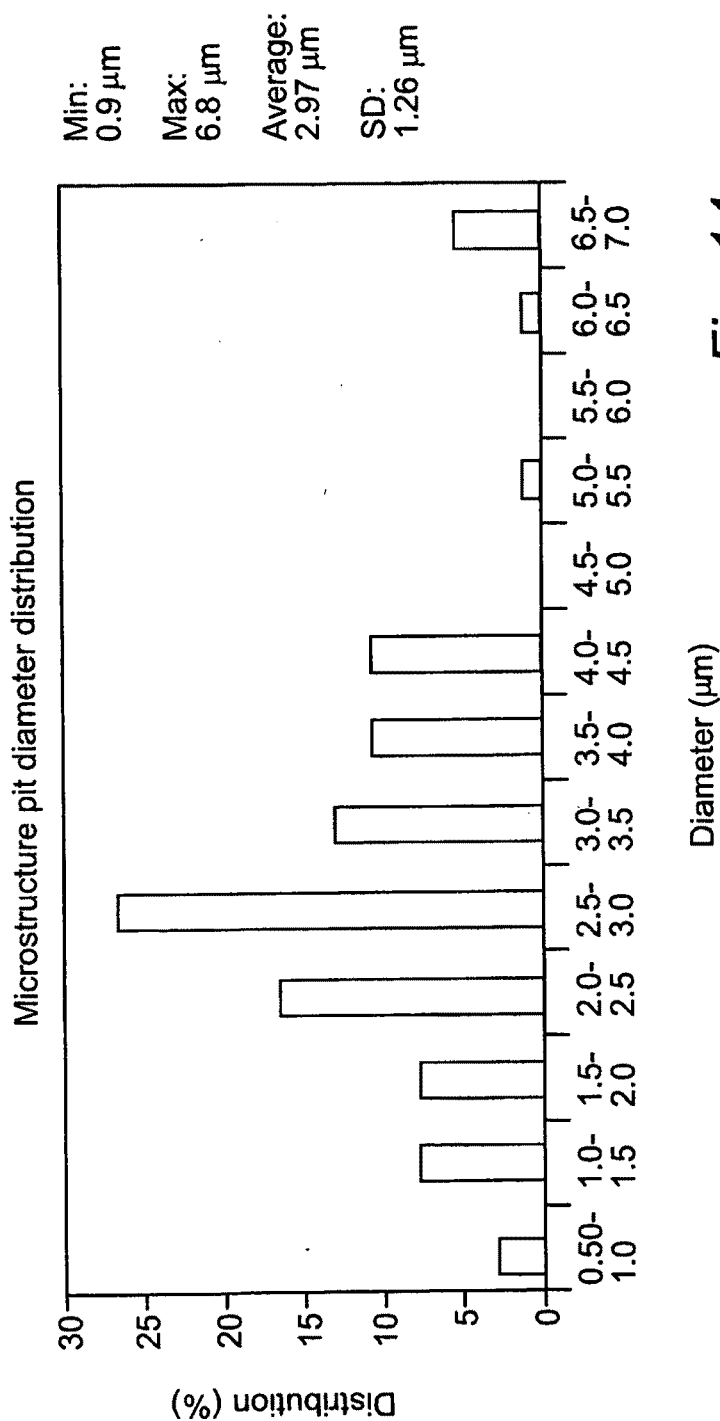
FIG. 14a-c are graphs showing the distribution of microstructure pit diameter, depth and distance between adjacent micropits, respectively, in a blasted titanium sample according to the invention.
Figure 14B:
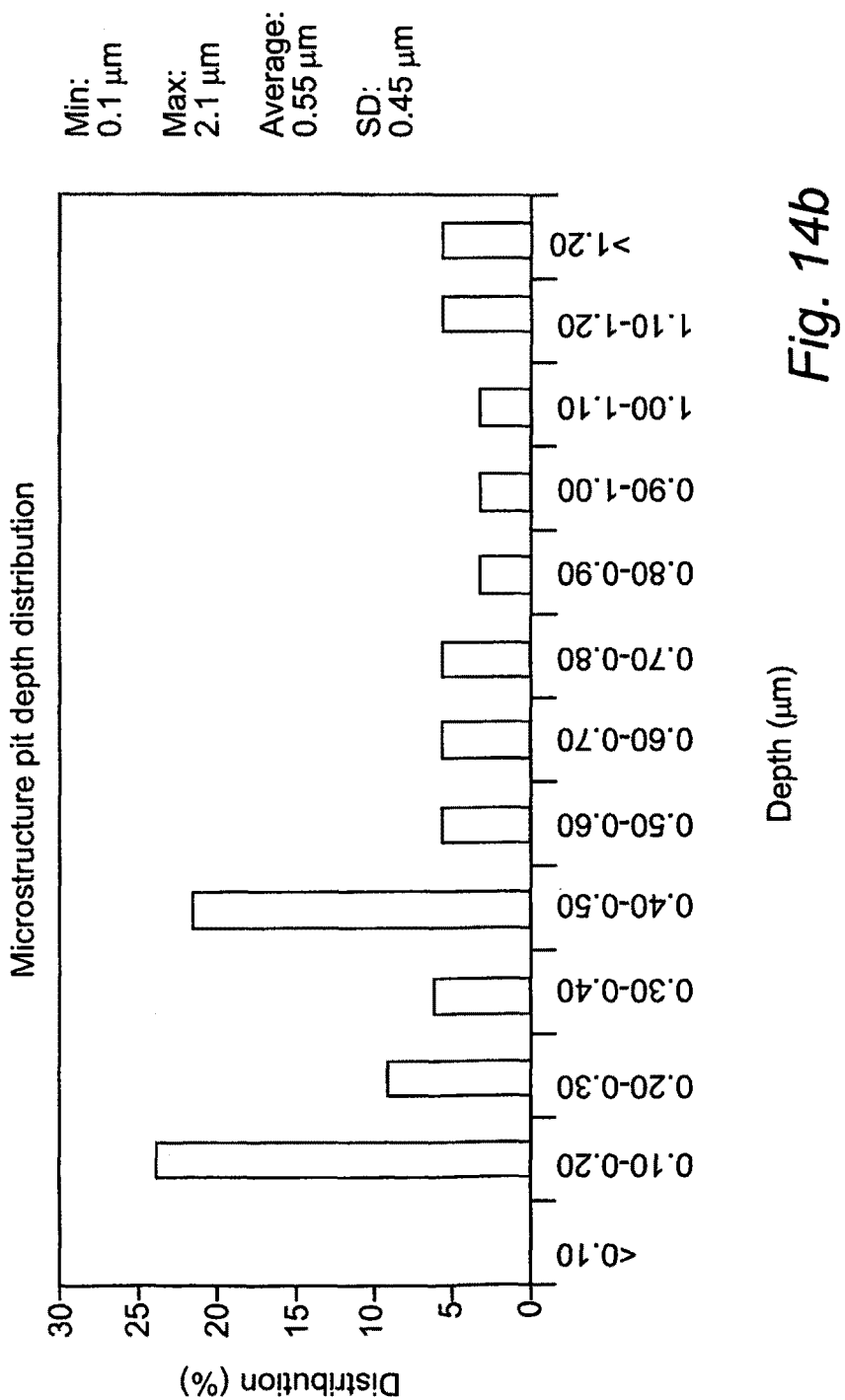
Figure 14C:
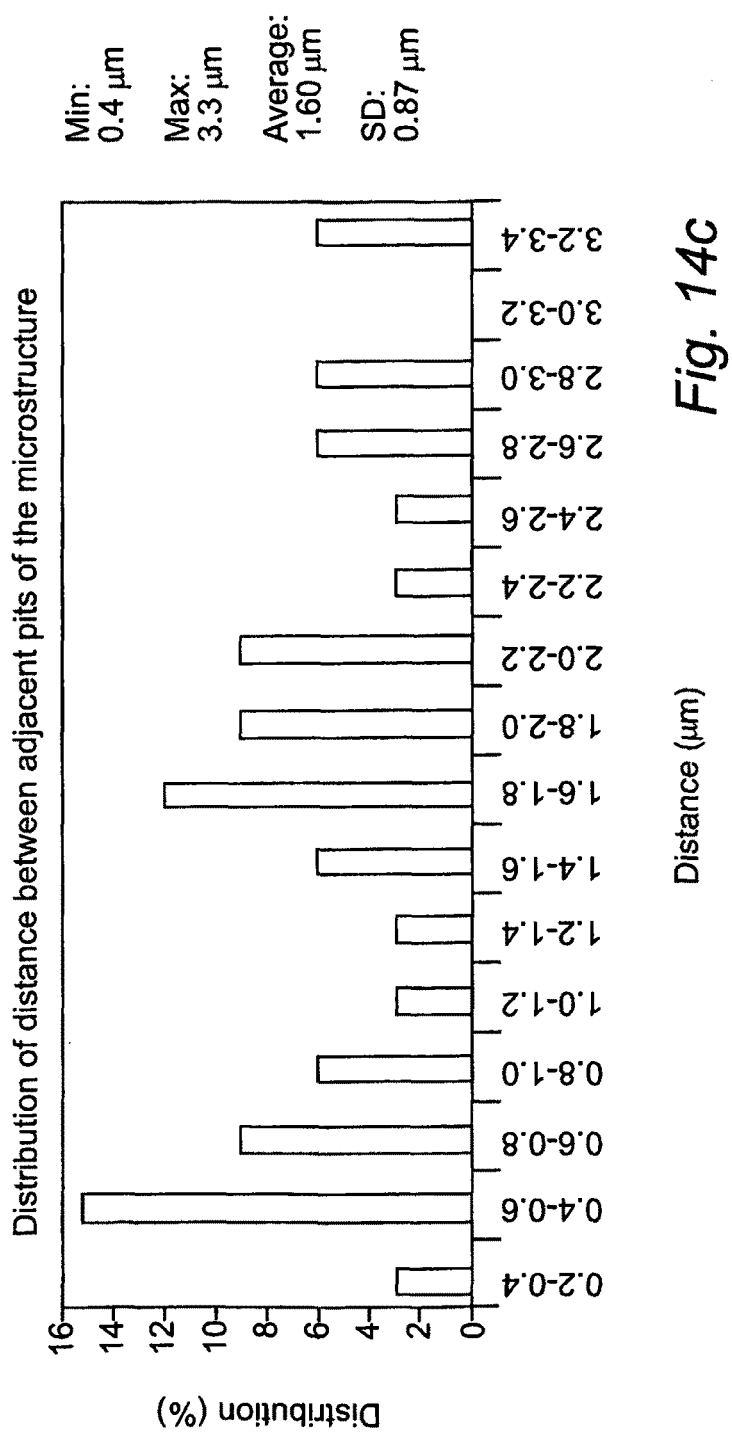

FIGS. 13 and 14 present the distributions of pit diameter, pit depth and distance between mutually adjacent pits of the microstructure. For example, a pit of the microstructure may have a diameter $x_1$ in the range of from 0.5 to 15 µm, preferably from 1 to 10 µm, and more preferably from 1 to 5 µm; and a depth $h_1$ in the range of 0.1 to 2.5 µm, preferably from 0.1 to 1 µm, and more preferably from 0.1 to 0.7 µm. Adjacent pits are typically separated by a plateau or a ridge, which may have a diameter of up to 10 µm, preferably up to 5 µm, and more preferably up to 3 µm. Thus, the distance $D_1$ between adjacent pits may be up to 10 µm, up to 5 µm, or up to 3 µm. However, as is often the case with a separating ridge, two adjacent pits may be considered not to be separated by any distance at all.

As seen in FIG. 5, the general shape of an individual pit of the microstructure may be roughly circular or oval, or it may be irregular. The microstructure may also comprise undercuts. Furthermore, a pit of a larger diameter may comprise one or several pits of a smaller diameter.

The microstructure may have an angle $\alpha$ as defined above and in FIG. 4 in the range of from 20° to 130°; preferably from 30° to 120°, more preferably from 40° to 110°, and most preferably from 50° to 100°.

Figure 15A:
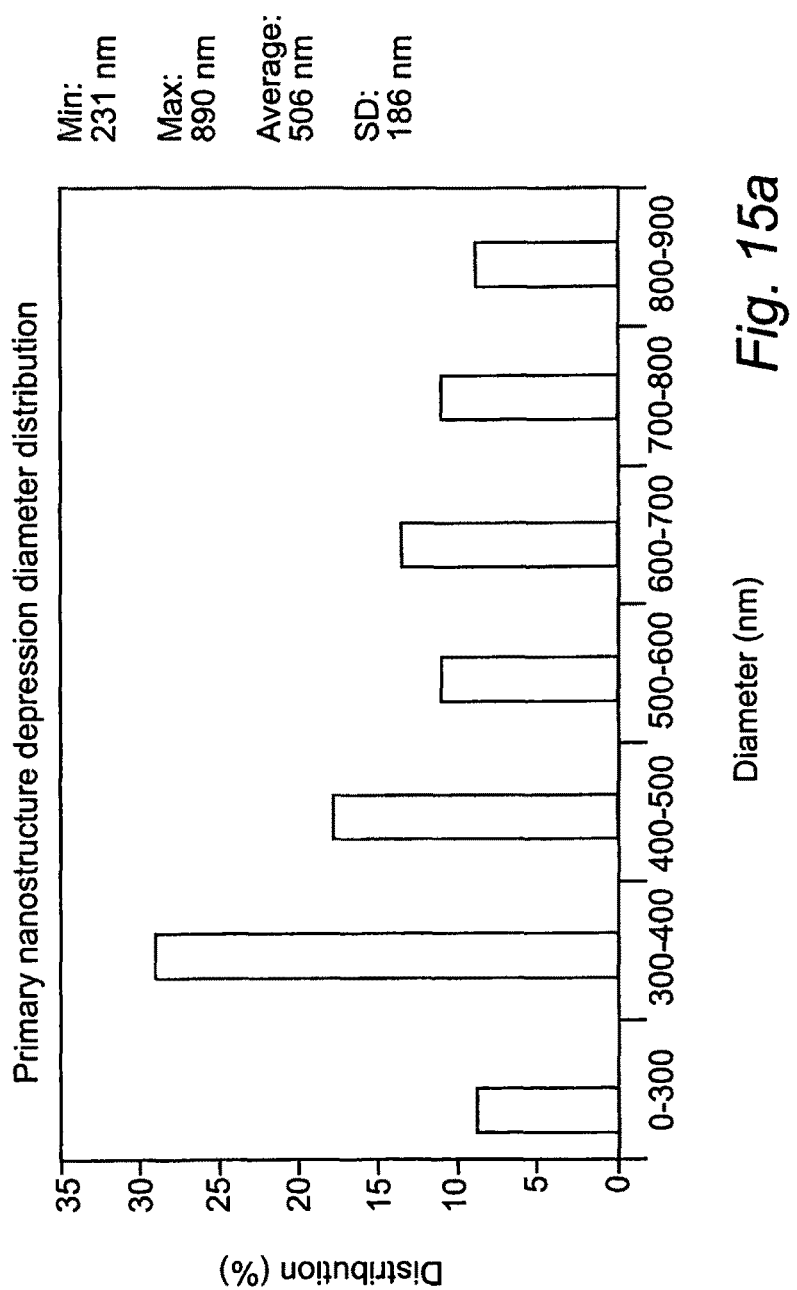
FIG. 15a-b are graphs showing the distribution of primary nanostructure depression diameter and depth, respectively, in a titanium sample according to the invention.
Figure 15B:
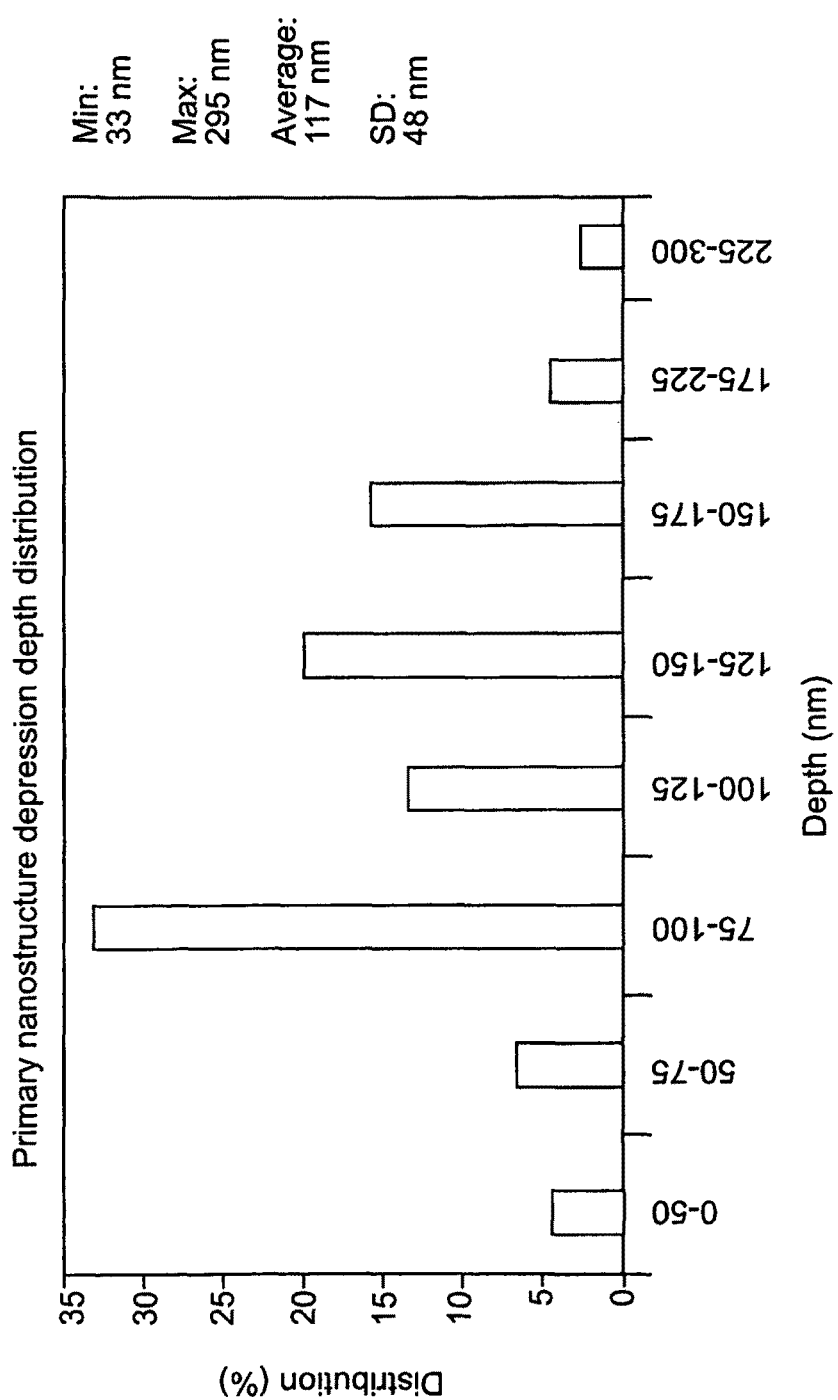
Figure 16A:
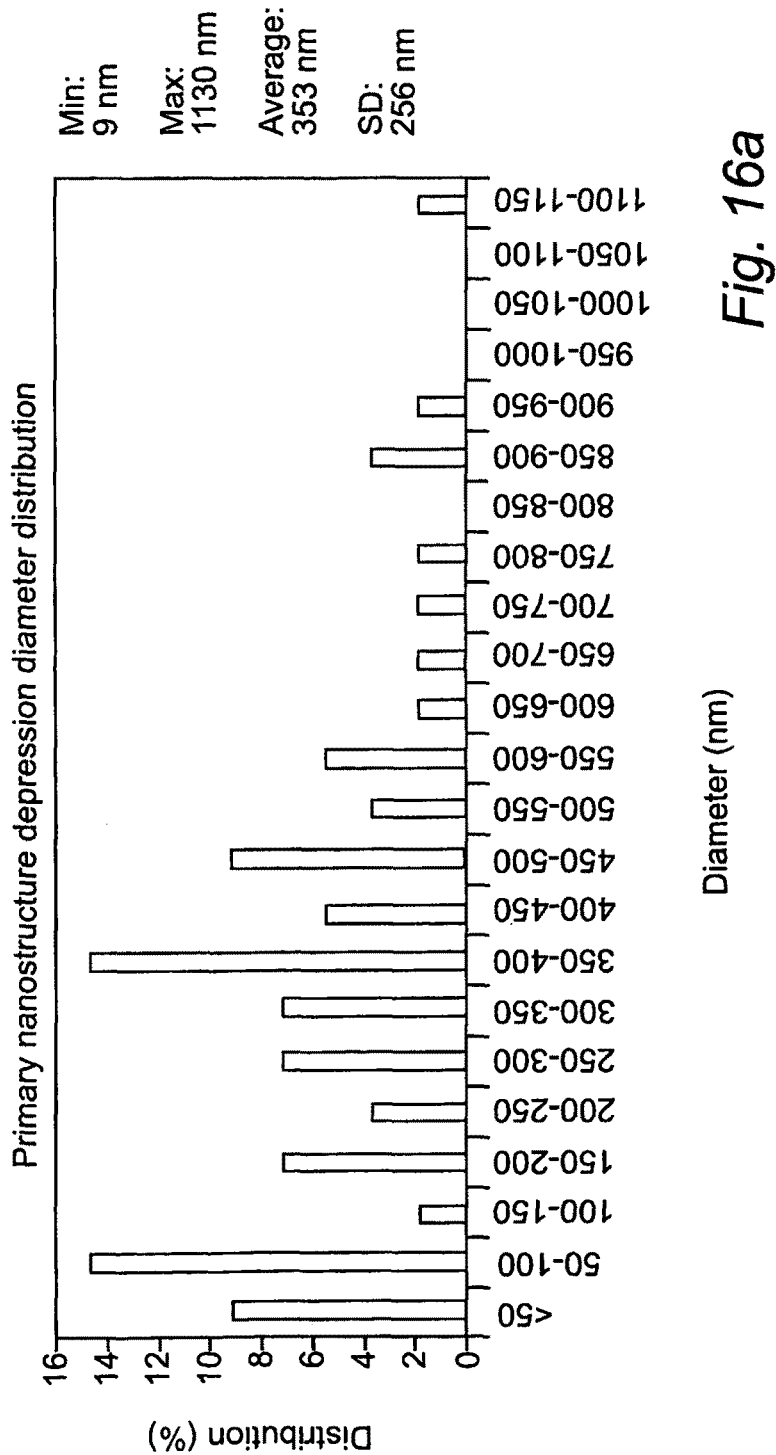
FIG. 16a-b are graphs showing the distribution of primary nanostructure depression diameter and depth, respectively, in a blasted titanium sample according to the invention.
Figure 16B:
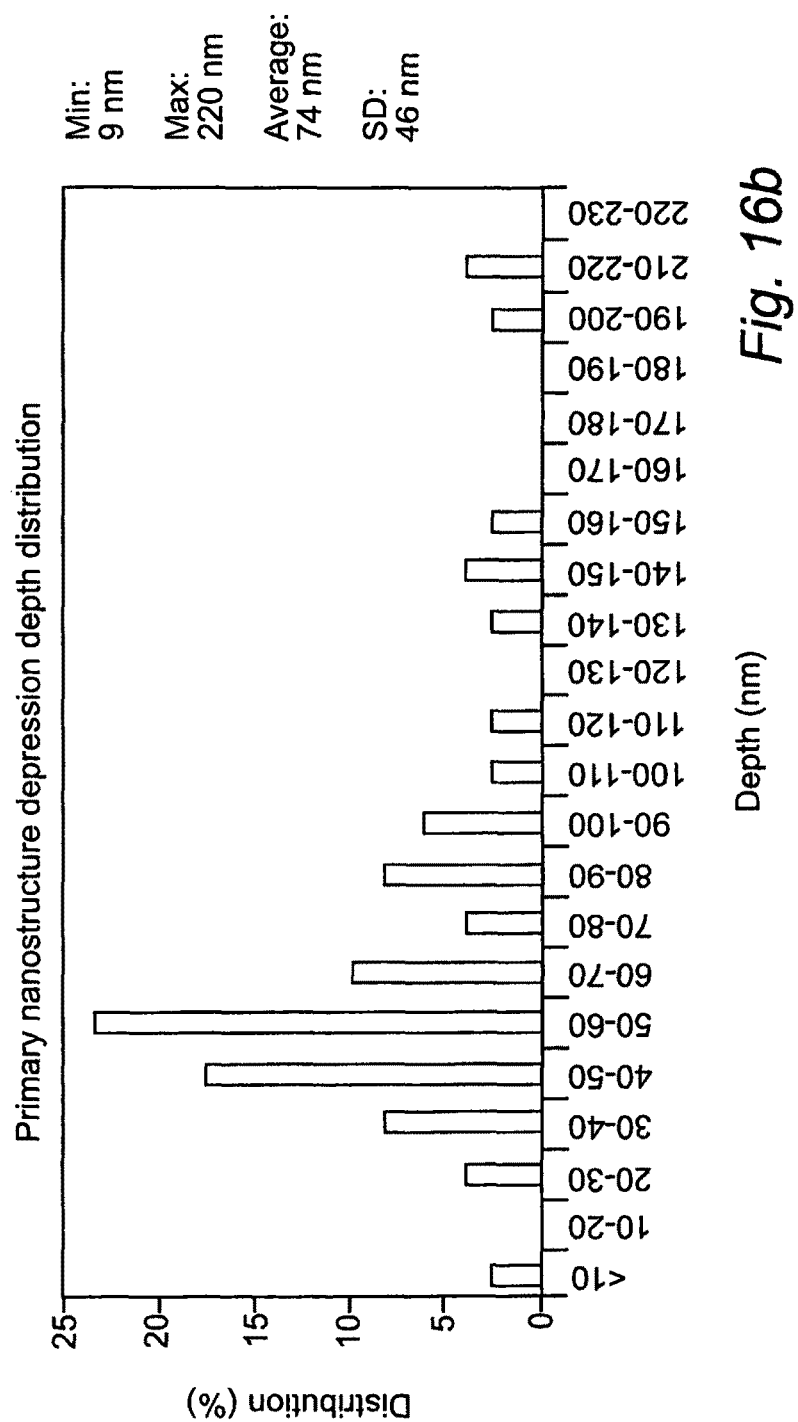

On the above described microstructure, a superimposed primary nanostructure is provided. The primary nanostructure may be seen in FIG. 5, and is further illustrated in FIG. 6, in which elements of the primary nanostructure have been marked. The primary nanostructure may be described as a wave-like continuous structure. The primary nanostructure comprises a multitude of shallow depressions in the walls and bottoms of the pits of the microstructure and in the plateaus and/or ridges separating the pits of the microstructure. The diameter $x_2$ of the depressions of the primary nanostructure may be in the range of from 10 nm to 1 µm, preferably from 10 nm to 600 nm, and more preferably from 10 nm to 500 nm; and the depth $h_2$ of the depressions of the primary nanostructure may be in the range of 10 to 300 nm, preferably from 30 to 150 nm. Typically the depressions are shallow, meaning that the diameter of a depression exceeds the depth thereof. The depressions of the primary nanostructure have an essentially circular or oval shape. FIGS. 15 and 16 present the diameter and depth distributions of the depressions of the primary nanostructure.

The depressions of the primary nanostructure may have a distinct boundary or edge. However, a depression of the primary nanostructure may also have a wall which rises from the bottom of said depression and then softly passes into the next depression without forming a distinct boundary therebetween. In either of the above cases, however, there is no definable distance separating the boundary of a depression of the primary nanostructure from the boundary of another depression. Rather, the depressions are juxtaposed to form a wave-like pattern having a quite regular aspect. The primary nanostructure may have an angle $\beta$ as defined above and in FIG. 4 in the range of from 80° to 160°; preferably from 90° to 150°, more preferably from 100° to 140°, and most preferably from 110° to 130°.

As mentioned above, the primary nanostructure is superimposed on the primary microstructure. Furthermore, the diameter and depth, respectively, of a primary nanostructure each is smaller than the corresponding dimension of an individual pit of the microstructure. Thus, an individual pit of the microstructure typically comprises multiple depressions of the primary nanostructure. For example, a pit of the microstructure may comprise from about 5 to about 50 of said depressions. Furthermore, a part of a boundary of a depression of the primary nanostructure typically constitutes a part of a boundary of another depression of the primary nanostructure.

Figure 10:
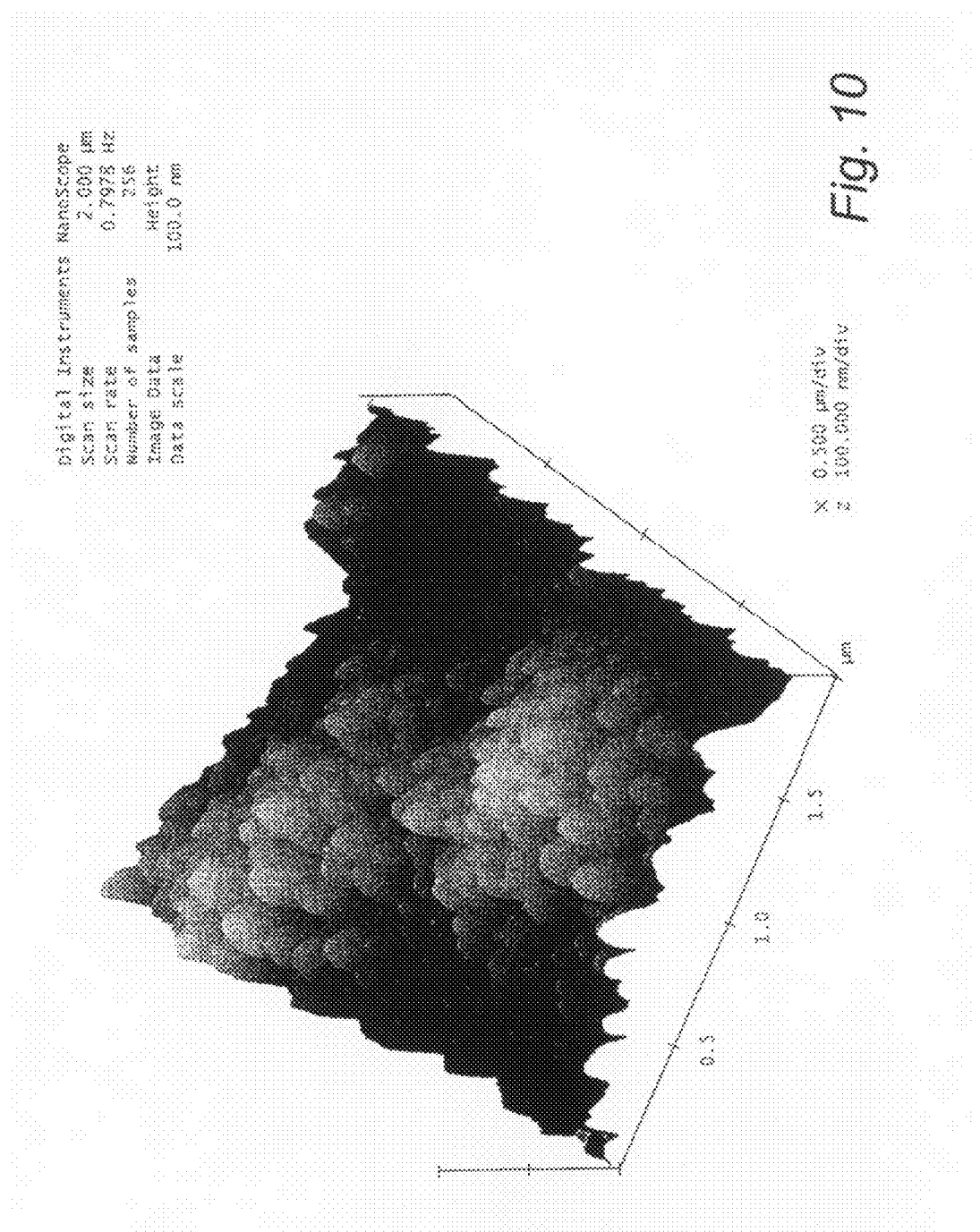
FIG. 10 is an atomic force microscopy 3D image of a titanium sample according to the invention.

FIG. 8 and FIG. 9 are SEM images of a modified component according to the invention. In FIG. 8, the sample was pretreated by blasting, whereas in FIG. 9, the sample was simply machine worked. In these figures, a secondary nanostructure which is superimposed on the above-mentioned microstructure and primary nanostructure can be seen. FIG. 10 is an image taken by atomic force microscopy (AFM) further illustrating the secondary nanostructure. As is seen in FIG. 10, the secondary nanostructure comprises discrete projecting elements having the shape of rounded peaks. The nanopeaks are densely and uniformly distributed on the underlying surface structure. For example, the number of peaks per unit area may be in the range of from 15 to 150 peaks/$\mu m^2$, and preferably from 50 to 130 peaks/$\mu m^2$.

Figure 11:
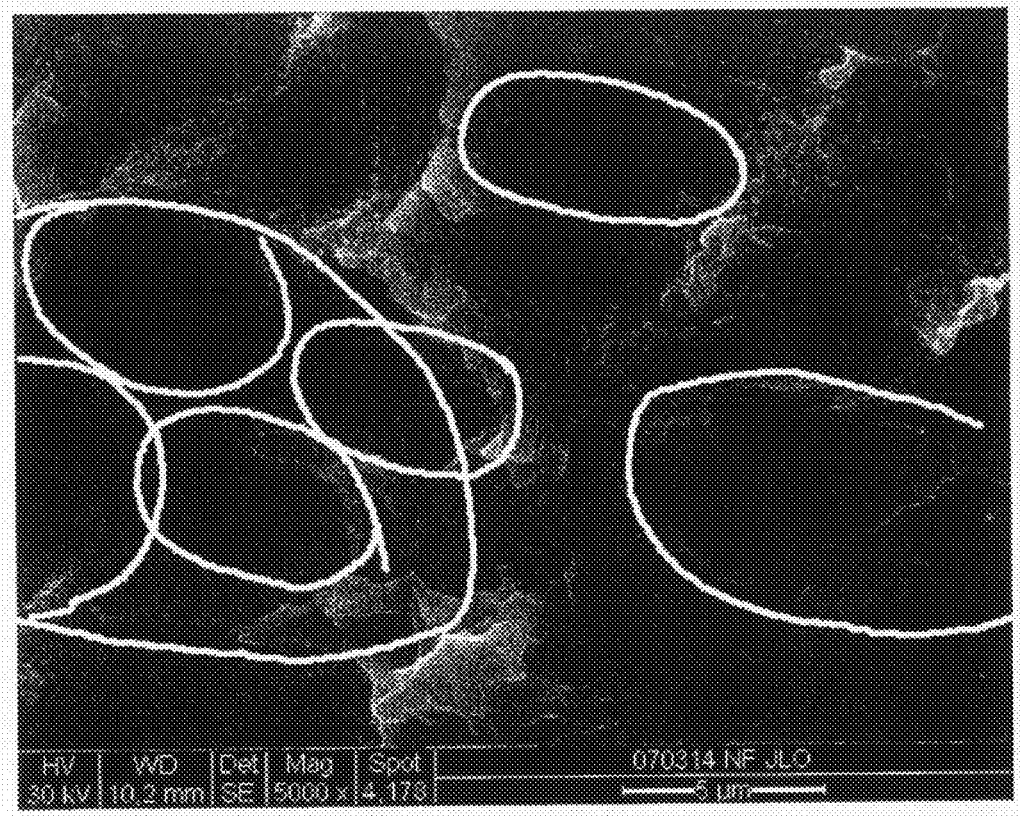
FIG. 11 is a scanning electron microscopy image of a blasted titanium sample according to the invention, wherein elements of the microstructure are marked.
Figure 17A:
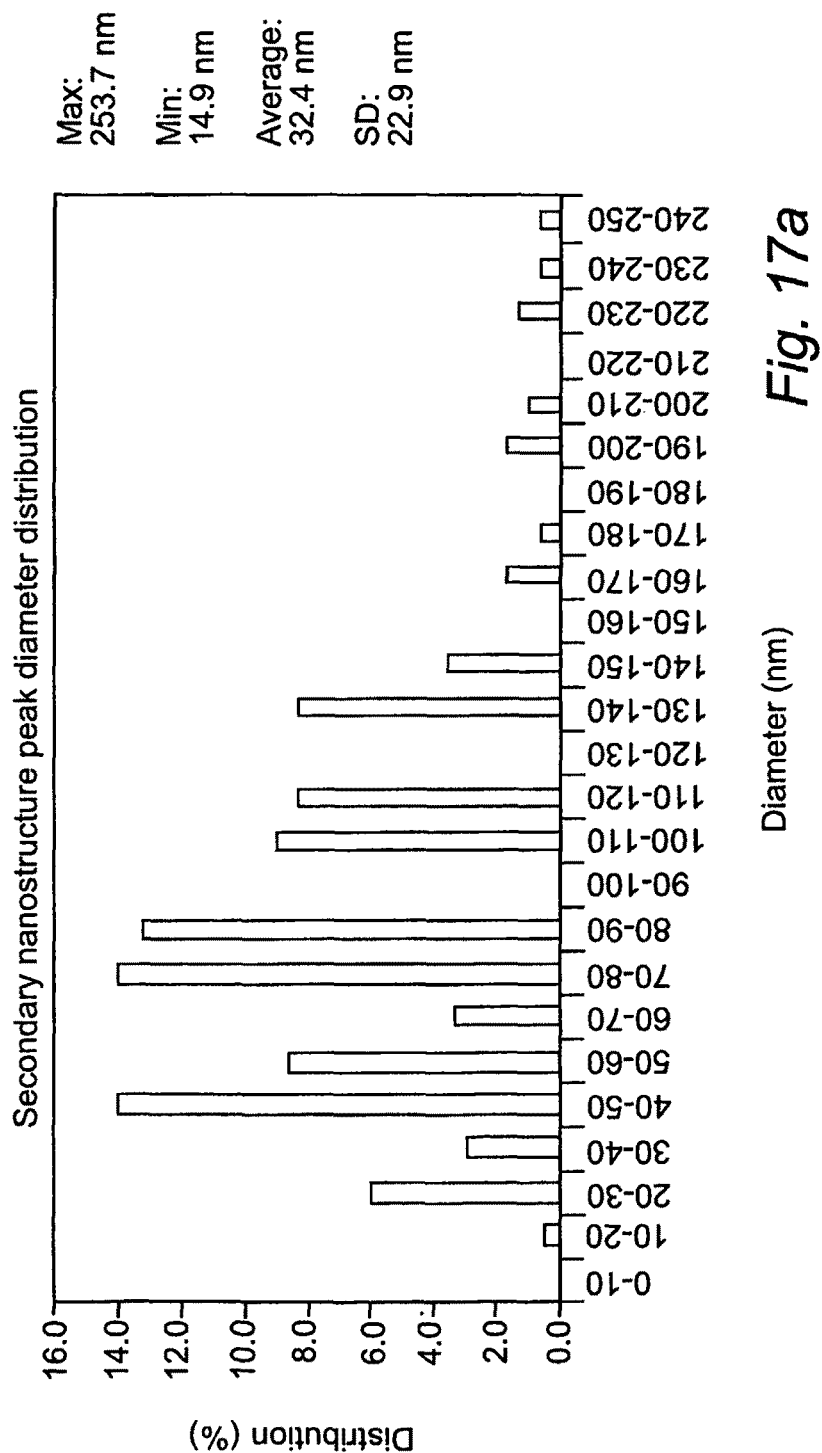
FIG. 17a-c are graphs showing the distribution of secondary nanostructure peak diameter, height and peak-to-peak distance, respectively, in a titanium sample according to the invention.
Figure 17B:
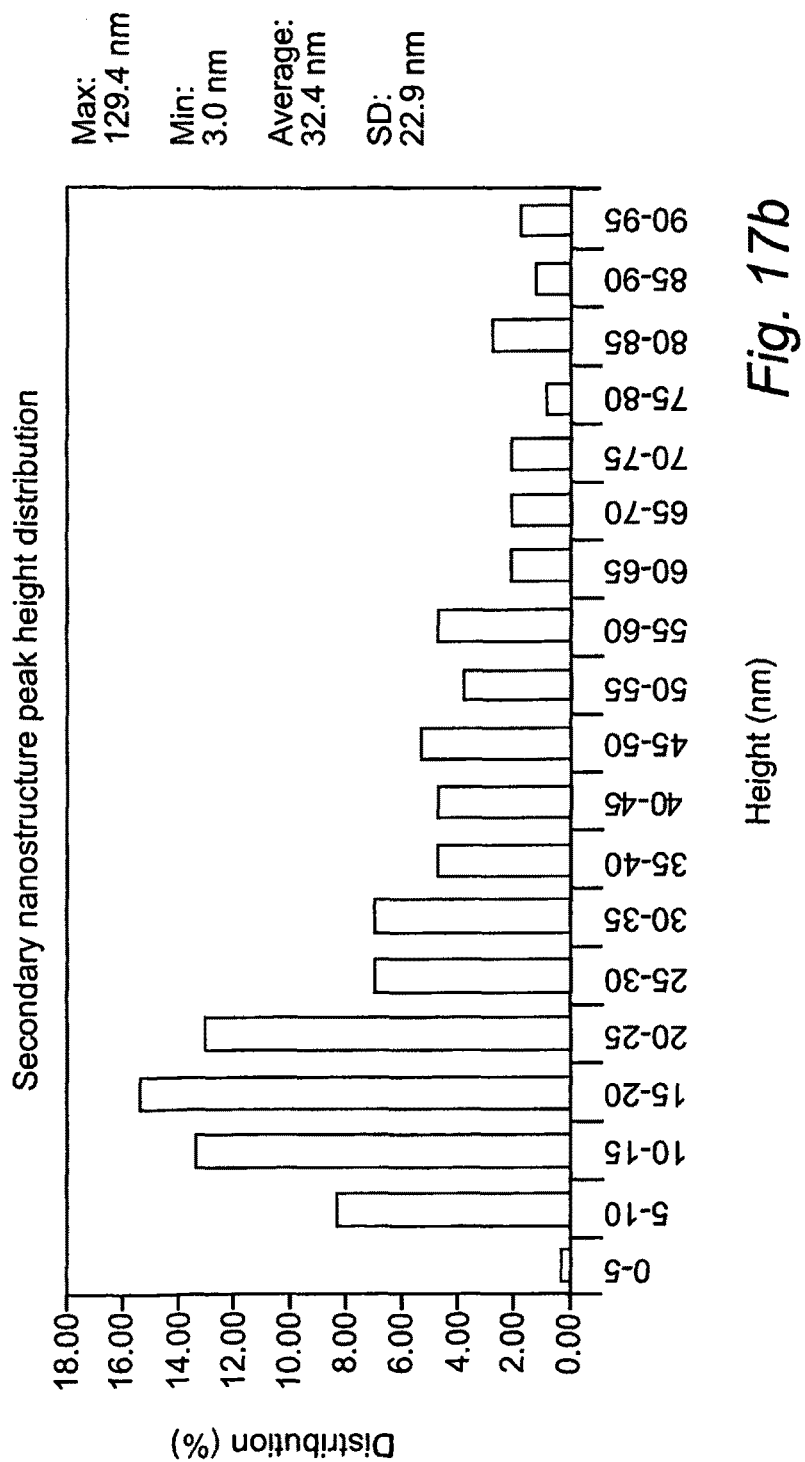
Figure 17C:
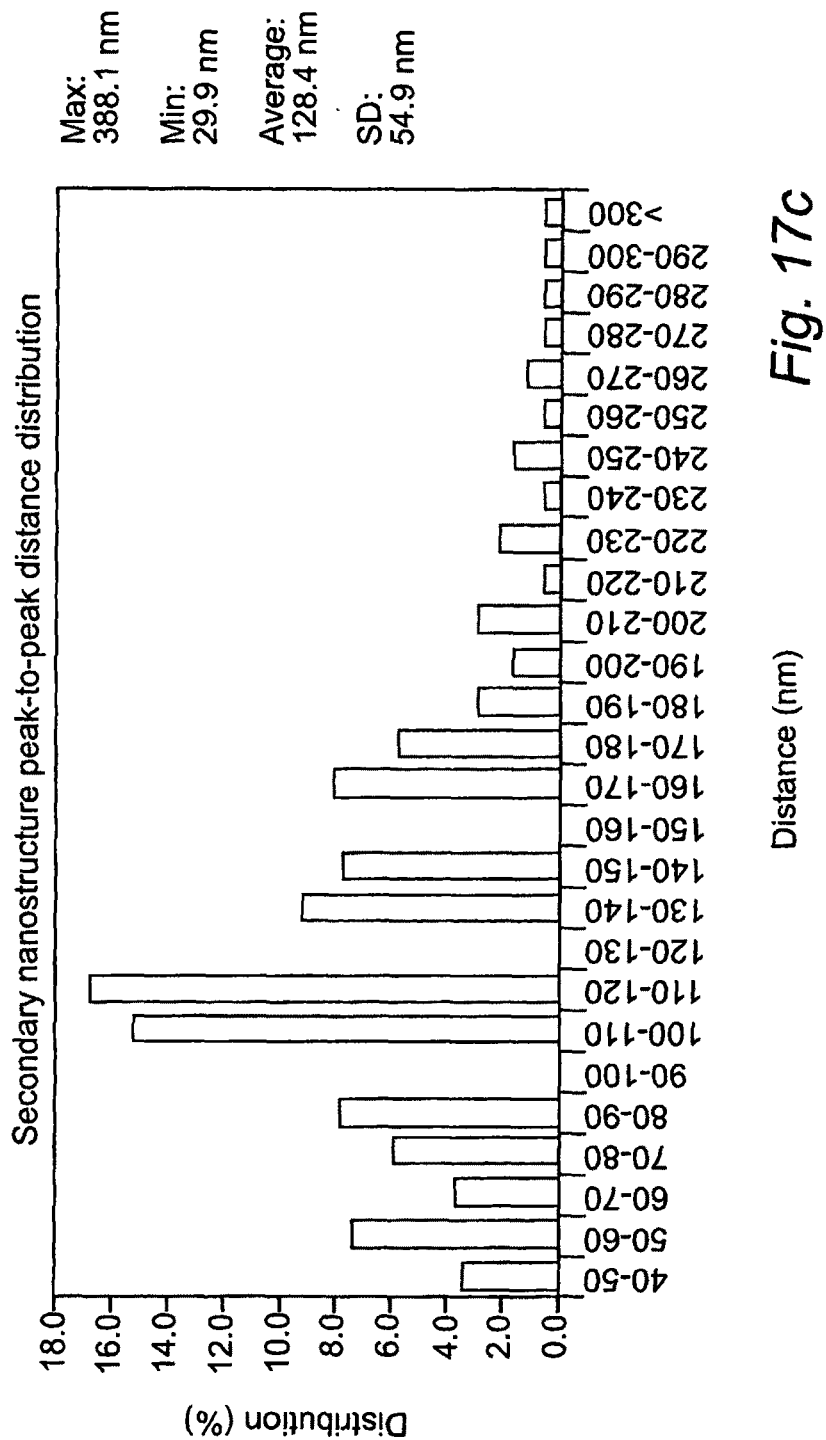

FIG. 17 presents the peak diameter, the average peak height and the peak-to-peak distance distributions of the secondary nanostructure Typically, the average peak height $h_3$ of the secondary nanostructure is in the range of from 5 to 200 nm, and preferably from 5 to 100 nm. The diameter $x_3$ of an individual peak of the secondary nanostructure typically is in the range of from 20 to 550 nm, and preferably from 20 to 150 nm. The peak-to-peak distance $D_3$ typically is in the range of from 10 to 450 nm, and preferably from 40 to 200 nm. FIG. 11 presents a SEM image of a component comprising the microstructure, the primary nanostructure and the secondary nanostructure, wherein pits of the microstructure have been marked.

Figure 7:
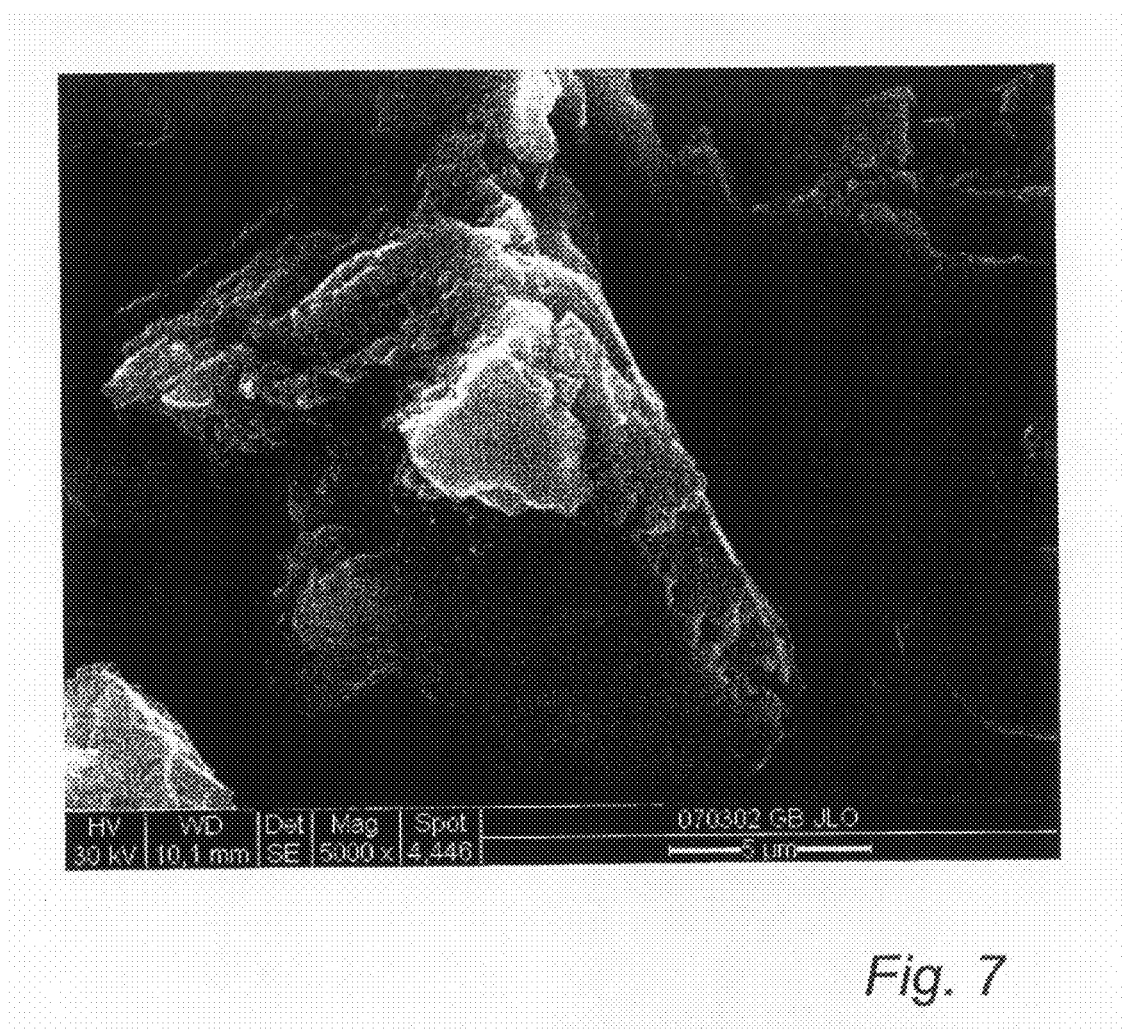
FIG. 7 is a is a scanning electron microscopy image of a titanium sample subjected to a conventional blasting technique.

In embodiments of the invention, in which a component of the invention has been subjected to blasting prior to the oxalic acid treatment, a superior surface structure exists on which the microstructure is superimposed. The surface structure of a component of the invention pretreated by blasting typically comprises large pits having a length in the range of from 10 to 70 μm and a depth in the range of from 3 to 20 μm. Typically, the large pits have a generally oval shape. The distance between adjacent pits may be in the range of from 1 to 20 μm. Superimposed on this large pit structure is the microstructure mentioned above. Thus, the sides and bottoms of the large pits and the surfaces between the large pits comprise the pits and the separating plateaus and/or ridges of the above mentioned microstructure. A SEM image of a conventional blasted surface is presented in FIG. 7. A blasting pretreatment affects the dimensions of the subsequently formed microstructure, primary nanostructure and optional secondary nanostructure. In a component according to the invention which was subjected to blasting, the subsequently formed microstructure generally had somewhat larger dimensions than the microstructure of a component according to the invention which was simply machine worked, and the subsequently formed primary nanostructure generally had somewhat smaller dimensions than the primary nanostructure of a component according to the invention which was simply machine worked. Additionally, the diameters of both the microstructure and the primary nanostructure, and the depths of the microstructure were more uniform in a blasted component, as is demonstrated by the standard deviation values shown in Table 1, than the corresponding features of a machine worked component.

In another aspect, the invention relates to a method for implanting a biocompatible component into the human or animal body. The method comprises the step of i) providing a biocompatible component as described above, and ii) implanting the component into the body of a human or an animal. For example, the biocompatible component may be implanted in a periodontal area of said body of a human or an animal.

EXAMPLES

Example 1

Surface Modification (i) Sample Preparation

Titanium samples having the shape of a coin (machine worked and blasted, respectively), a fixture (blasted) and an abutment (machine worked) were cleaned by a conventional chemical treatment. The samples were immersed in an 1 M aqueous solution of oxalic acid and left at 80° C. for 30 minutes under vigorous agitation. After 30 minutes the samples were removed from the oxalic acid solution and rinsed in water followed by rinsing in water in an ultrasonic bath for 2 minutes. Approximately 10 minutes after rinsing, the samples were immersed in 0.1 M aqueous solution of hydrofluoric acid (HF) at room temperature and agitation until the start of active dissolution, followed by an additional active treatment time of 40 seconds. Next, the samples were removed from the HF solution and rinsed in water followed by rinsing in water in an ultrasonic bath for 5 minutes. The samples were dried in air at room temperature for about 60 minutes before sterilisation.

(ii) Surface Topology Measurements

Scanning electron microscopy (SEM) was performed using ESEM XL 30 (FEI) on samples after rinsing following step b and after drying following step c. Stereo images using magnifications between 500× and 15000× were taken and evaluated by the MeX 5.0 programme (Alicona). No filters were used. Depths and diameters of the pits of the microstructure and the depressions of the primary nanostructure and distances between adjacent pits of the microstructure were determined. The results are presented in FIG. 13a-c (machine worked sample) and FIG. 14a-c (blasted sample) for the primary microstructure and in FIG. 15 a-b (machine worked sample) and FIG. 16 a-b (blasted sample) for the primary nanostructure. SEM images taken after step b are presented in FIGS. 5a-b and 6a-b. SEM images taken after sterilisation are presented in FIGS. 8, 9 and 11.

TappingMode™ atomic force microscopy (AFM) was performed using a Nanoscope IIIa instrument (Digital Instruments). The secondary nanostructure of three samples according to the invention (machine worked) were analysed at two points per sample, each point located approximately 1 mm from the sample edge. The area of analysis was 2 μm×2 μm. Peak heights, peak diameters, peak-to-peak distances and the number of peaks/$\mu m^2$ were determined. Said dimensions were measured in mm and converted to nm using the scale provided in the profile plots obtained. The distributions of peak height, peak diameter and peak-to-peak distance, respectively, are presented in FIG. 17a-c.

Table 1 summarizes the maximum, minimum and average values of the dimensions determined for the microstructure and primary nanostructure for blasted and machine worked components, respectively, determined by SEM/MeX 5.0. The maximum, minimum and average values determined for the secondary nanostructure of a machine worked component by AFM are also presented.

TABLE 1

Surface structure dimensions for blasted and machine worked samples according to the invention.

| | | Blasted sample | Machine worked sample |
|---|---|---|---|
| Microstructure | | | |
| Diameter ($x_1$) (μm) | max | 6.8 | 9.83 |
| | min | 0.9 | 3.74 |
| | average | 2.97 | 2.24 |
| | SD | 1.26 | 1.59 |
| Depth ($h_1$) (μm) | max | 2.1 | 1.27 |
| | min | 0.1 | 0.01 |
| | average | 0.55 | 0.34 |
| | SD | 0.45 | 0.25 |
| Distance ($D_1$) (μm) | max | 3.3 | 7.99 |
| | min | 0.4 | 0.0 |
| | average | 1.60 | 1.54 |
| | SD | 0.87 | 1.44 |
| Primary nanostructure | | | |
| Diameter ($x_2$) (nm) | max | 1130 | 890 |
| | min | 9 | 231 |
| | average | 353 | 506 |
| | SD | 256 | 186 |
| Depth ($h_2$) (nm) | max | 220 | 295 |
| | min | 9 | 33 |
| | average | 74 | 117 |
| | SD | 46 | 48 |
| Secondary nanostructure | | | |
| Diameter ($x_3$) (nm) | max | n/a | 253.7 |
| | min | n/a | 14.9 |
| | average | n/a | 32.4 |
| | SD | n/a | 22.9 |
| Height ($h_3$) (nm) | max | n/a | 129.4 |
| | min | n/a | 3.0 |
| | average | n/a | 32.4 |
| | SD | n/a | 22.9 |
| Peak-to-peak distance ($D_3$) (nm) | max | n/a | 388.1 |
| | min | n/a | 29.9 |
| | average | n/a | 128.4 |
| | SD | n/a | 54.9 |

Comparative Example 1a

Blasted titanium samples (coin-shaped) were immersed in an aqueous solution comprising 0.1 M hydrofluoric acid and 1 M oxalic acid at room temperature and agitation for 5, 15, 30 and 42 minutes, respectively. The samples were removed from the solution and rinsed in water followed by rinsing in water in an ultrasonic bath for 2 minutes. After drying of the samples, the surface topography was examined by scanning electron microscopy (ESEM XL 30, FEI).

Figure 12A:
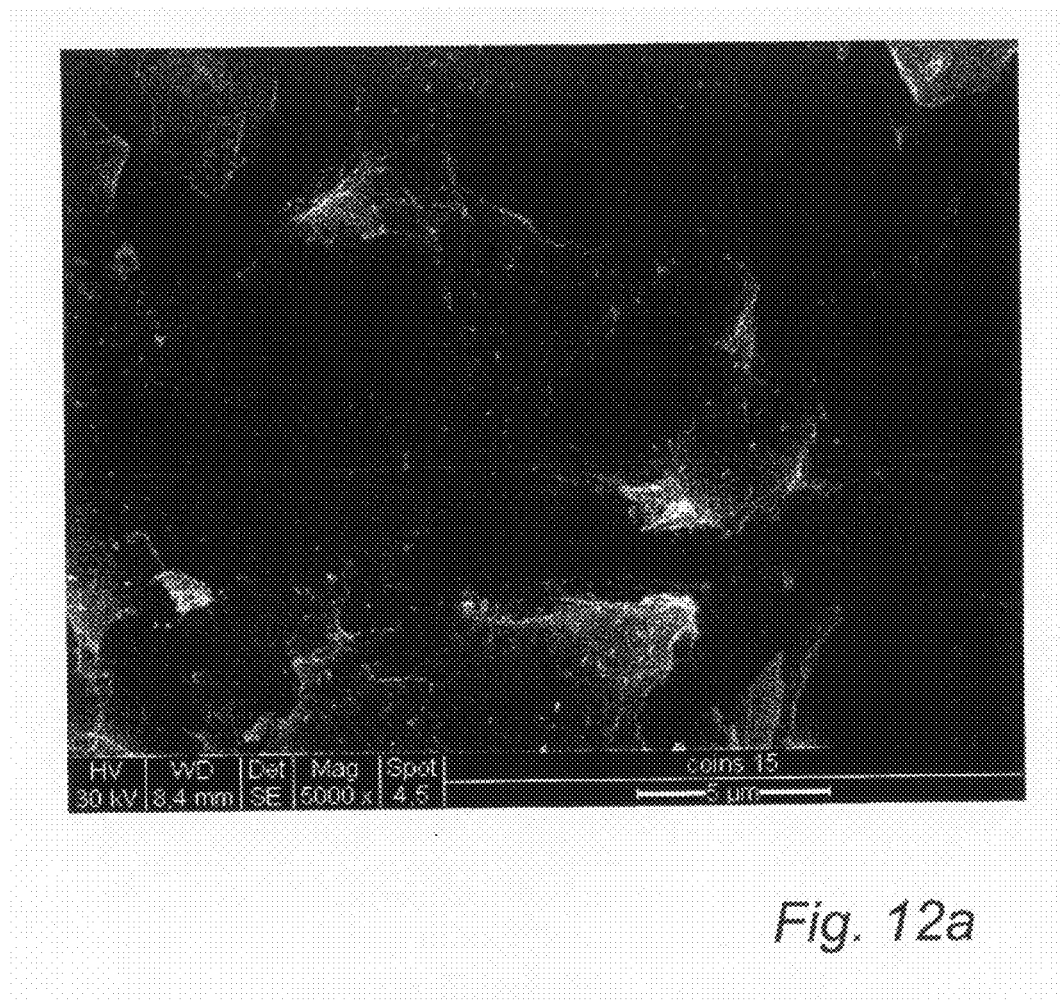
FIG. 12a-b are scanning electron microscopy images of a titanium reference sample treated in a mixture of hydrofluoric acid and oxalic acid.
Figure 12B:
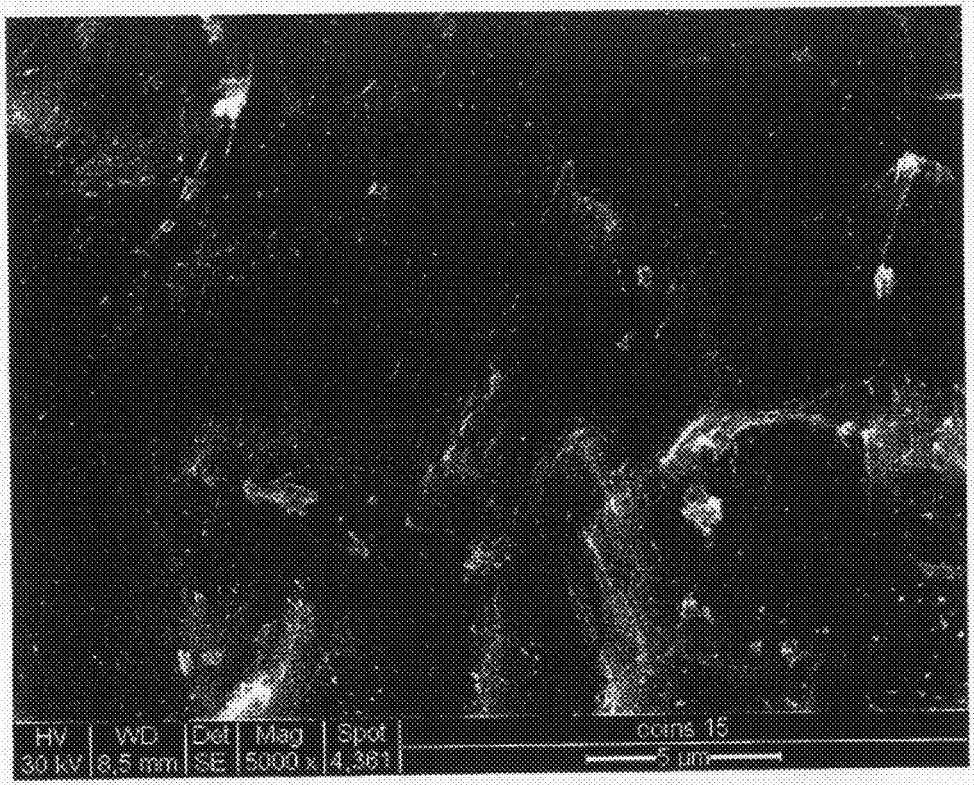

As a result, 5 minutes of the above treatment yielded samples having partly etched regions and non-uniformly distributed projecting elements. Samples taken after 15 minutes exhibited a relatively flat, etched surface structure comprising sparsely projecting elements. The surface of samples taken after 30 minutes had a striped appearance and comprised small projecting elements and also some unidentified particles. A SEM image of a dried sample treated for 5 minutes is presented in FIG. 12a, and a SEM image of a dried sample treated for 30 minutes is presented in FIG. 12b.

Comparative Example 1b

Titanium samples were immersed in a 0.1 M aqueous solution of HF at room temperature and agitation until the start of active dissolution, followed by an additional treatment time of 40 s. Next, the samples were removed from the HF solution and rinsed in water followed by rinsing in water in an ultrasonic bath for 5 minutes. Approximately 10 minutes after rinsing the samples were immersed in an 1 M aqueous solution of oxalic acid and left at 80° C. for 30 minutes under vigorous agitation. After 30 minutes the samples were removed from the oxalic acid solution and rinsed in water followed by rinsing in water in an ultrasonic bath for 2 minutes. The samples were allowed to dry for 1 hour at room temperature.

Figure 12C:
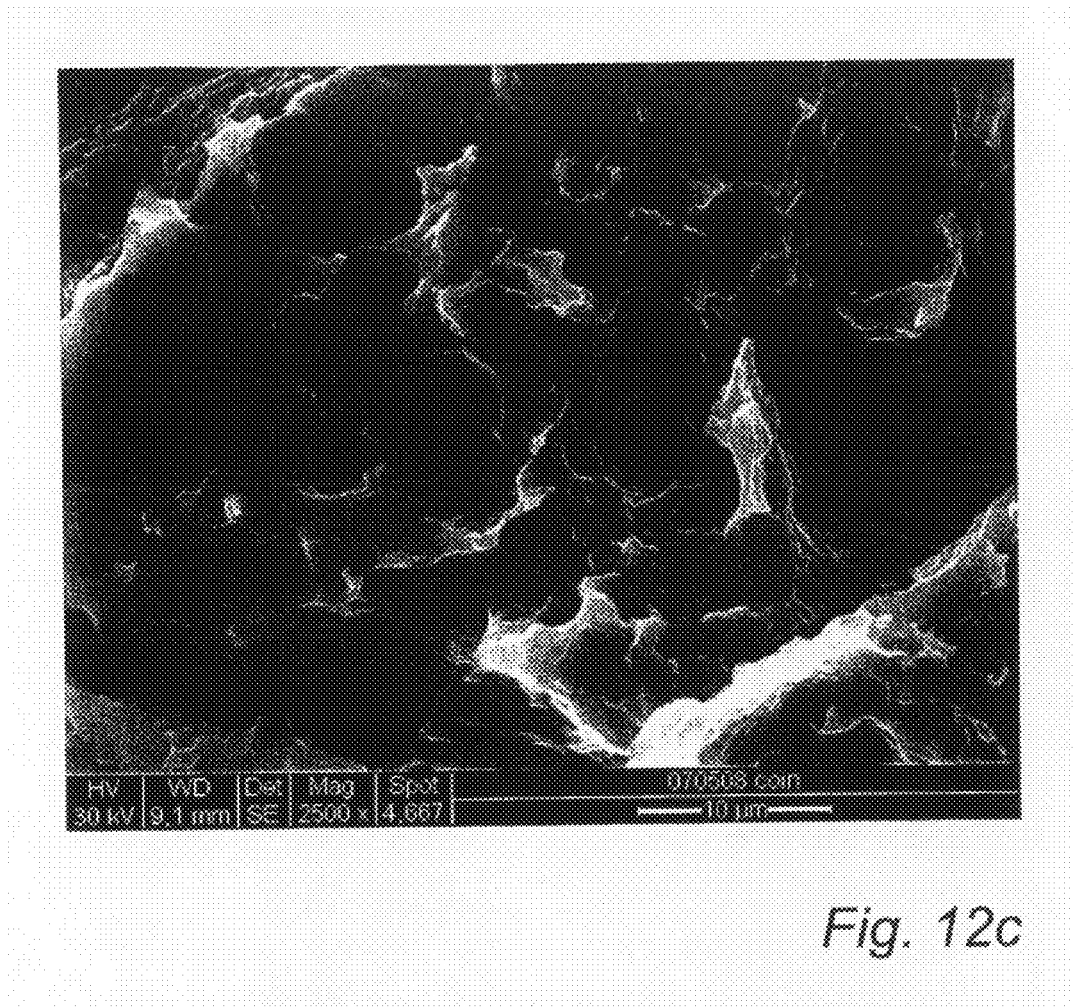
FIG. 12c is a scanning electron microscopy image of a titanium sample treated in hydrofluoric acid and subsequently in oxalic acid.

An image were taken of a dried sample by scanning electron microscopy (ESEM XL 30, FED. The result is presented in FIG. 12c.

Example 2

Cell Proliferation and Activity

Cell proliferation and production of alkaline phosphatase (ALP) and prostaglandin E2 (PGE2), respectively, was investigated for human osteoblast cells grown in vitro on titanium surfaces according to the invention in comparison to cells grown on a commercial implant surface (OsseoSpeed™; Asta Tech AB, Sweden).

(i) Cell Cultivation

MG-63 is a human cell line conventionally used for in vitro studies of osteoblasts. In this study, MG-63 cells (MG-63, ATCC No CRL-1427, U.S.) were grown in 300 ml Falcon cell culture flasks (BD, WWR, Sweden) in Dulbecco's Minimun Essential Medium (D-MEM) (Gibco, UK) containing 5% fetal calf serum (FCS; Gibco, UK) and 1% penicillin-streptomycin (PEST; Gibco, UK) from second passage from an ampulla of frozen cells. When adherent cells had grown to confluency, they were passaged using 0.05% Trypsin-EDTA (Gibco, UK) for 3 passages. Cell viability was high (>98%) as counted using light microscopy.

(ii) Cell Morphology (SEM)

Figure 20A:
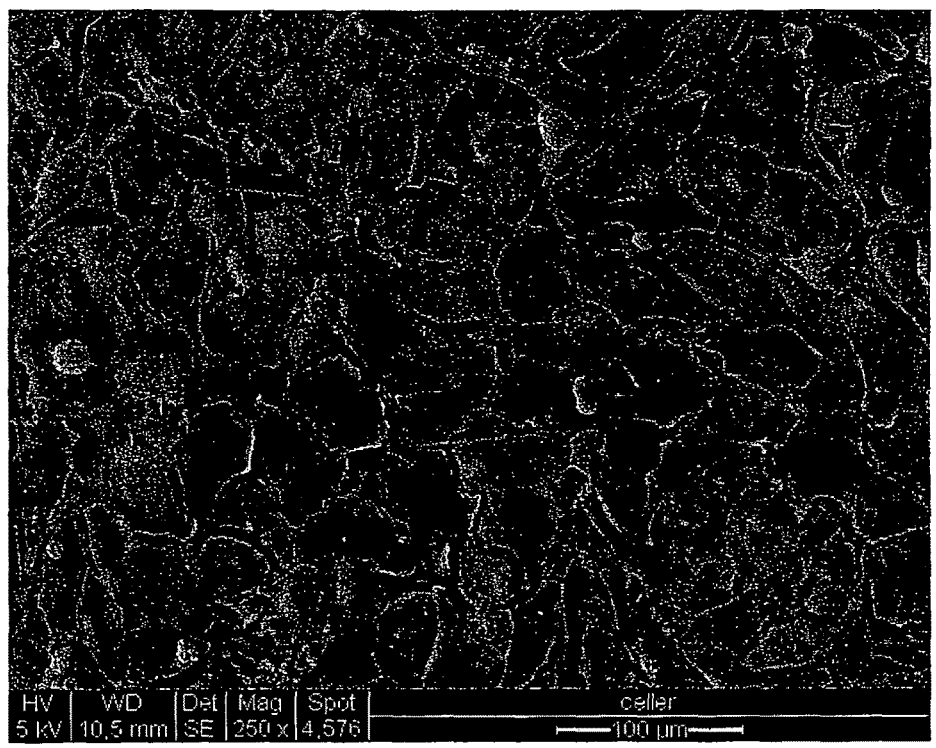
FIG. 20a is a scanning electron microscopy image of cells grown for 36 hours centrally on a commercial implant surface.

Three coin-shaped β-sterilised titanium sample bodies, one of which had been subjected to step b according to the invention, one of which had been subjected to step b and step c according to the invention and one of which had a commercially available surface (OsseoSpeed™; Asta Tech AB, Sweden) were each placed in a separate Falcon 24 well plate (BD, WWR, Sweden). To each well was added 1 ml D-MEM (Gibco, UK) containing 5% FCS (Gibco, UK) and 1% PEST (Gibco, UK) having a cell concentration of 20 000 cells/ml. The plates were incubated at 37° C., 5% $CO_2$ and 100% humidity for 36 hours. Samples were fixed using glutaraldehyde at 4° C., followed by osmium tetroxide fixation, dehydration and gold sputtering according to a conventional SEM sample preparation procedure. Cell morphology was investigated by SEM (ESEM XL 30, FED. SEM images of the cells are shown in FIG. 20a (cells grown on a conventional surface), FIG. 20b (cells grown on a component treated according to step b of the invention) and in FIG. 20c (cells grown on a component treated according to step b and step c of the invention).

(iii) Evaluation of Cell Proliferation, ALP Activity and PGE2 Activity

Three sets (n=6) of coin-shaped p-sterilised titanium sample bodies, one set having been subjected to step b according to the invention ("Inventive surface 1"), one set having been subjected to step b and step c according to the invention ("Inventive surface 2"), and one set having a commercially available surface (OsseoSpeed™; Asta Tech AB, Sweden), were each placed in a separate Falcon 24 well plate (BD, WWR, Sweden). To each well was added 1 ml D-MEM (Gibco, UK) containing 5% FCS (Gibco, UK) and 1% PEST (Gibco, UK) and having a MG-63 cell concentration of 20 000 cells/ml. The plates were incubated at 37° C., 5% $CO_2$ and 100% humidity for 14 days.

Figure 19:
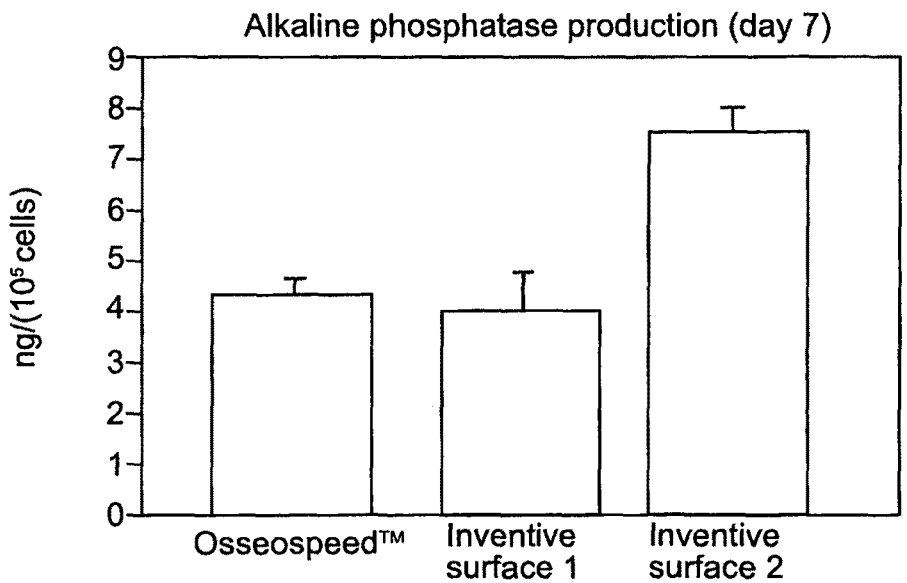
FIG. 19 is a graph showing the production of alkaline phosphatase after 7 days of cell cultivation on a commercial titanium implant surface and on surfaces according to the invention, respectively.

After 7 days of cultivation, a sample (50 from each well was analysed for exogeneous ALP. Adherent cells were analysed for endogeneous ALP by cell lysis followed by centrifugation and determination of supernatant and intracellular ALP content (ng/ml) using SenzoLyte™ pNPP Alkaline Phosphatase Assay Kit Colorimetric (BioSite, Sweden) according to the instructions of the manufacturer. After 7 days, the samples subjected to both step b and step c according to the invention (Inventive surface 2) had induced a markedly higher production of ALP per cell than the reference samples (OsseoSpeed™). The results are presented in FIG. 19.

Figure 18:
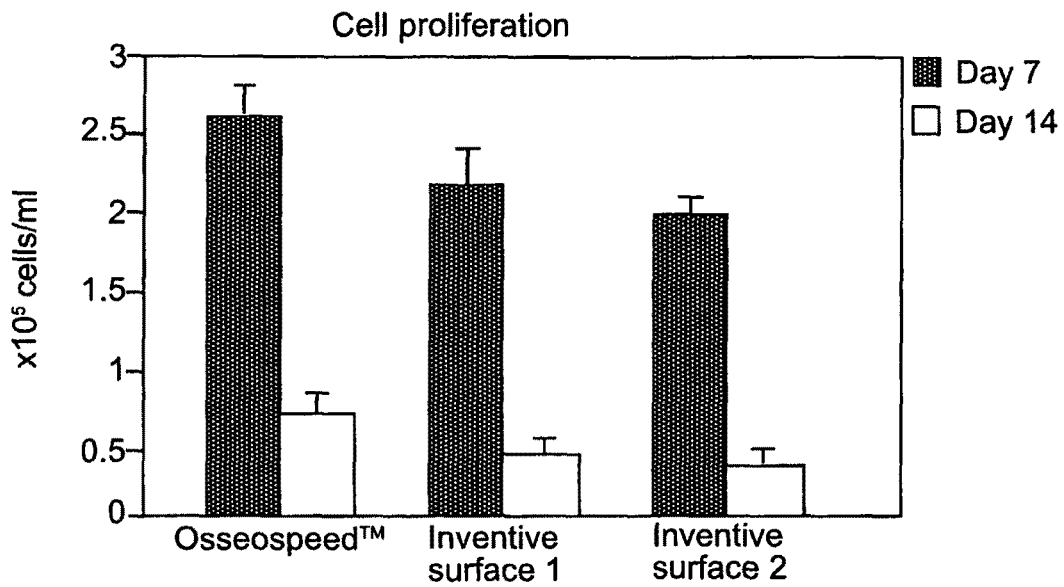
FIG. 18 is a graph showing the proliferation of cells grown for 7 days on a commercial titanium implant surface and on surfaces according to the invention, respectively.

After 7 and 14 days of cultivation, respectively, the total number of cells/well was determined using NucleoCassette, NucleoCounter (ChemoMetec A/S Denmark) according to the instructions of the manufacturer. The results are presented in FIG. 18.

Figure 21:
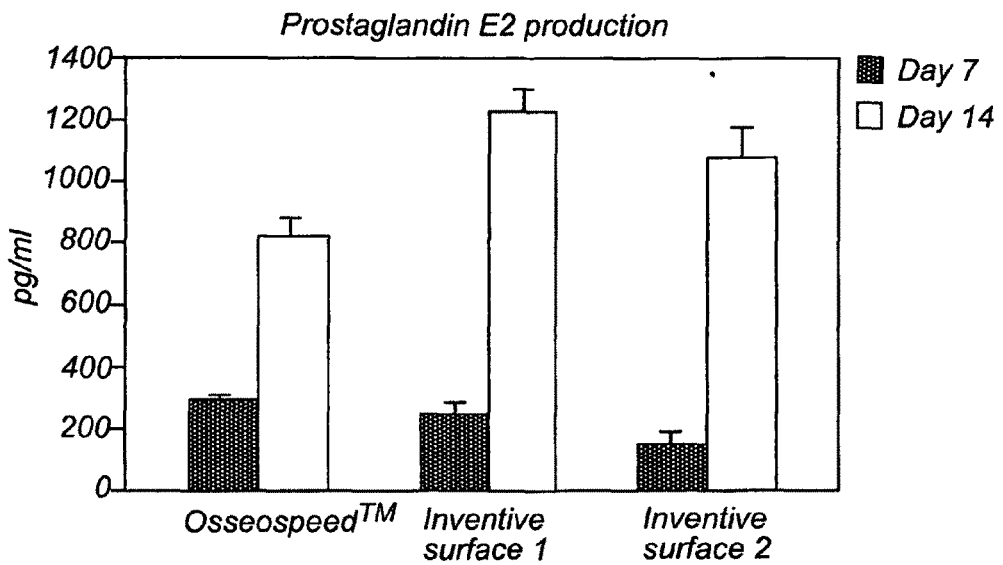
FIG. 21 is a graph showing the production of prostaglandin E2 after 7 and 14 days of cell cultivation on a commercial titanium implant surface and on surfaces according to the invention, respectively.

After 7 and 14 days of cultivation, respectively, 300 μl of supernatant from each well was used for determination of PGE2 using ELISA kit R&D Systems PGE2 Immunoassay (R&D Systems, UK) according to the instructions of the manufacturer. After 7 days of cultivation, the production of PGE2 was slightly lower in the samples according to the invention compared to the reference. After 14 days, however, both sets of samples according to the invention had induced a markedly higher production of PGE2 per cell than the reference samples. The results after 7 and 14 days of cultivation, respectively, are presented in FIG. 21.

Figure 20B:
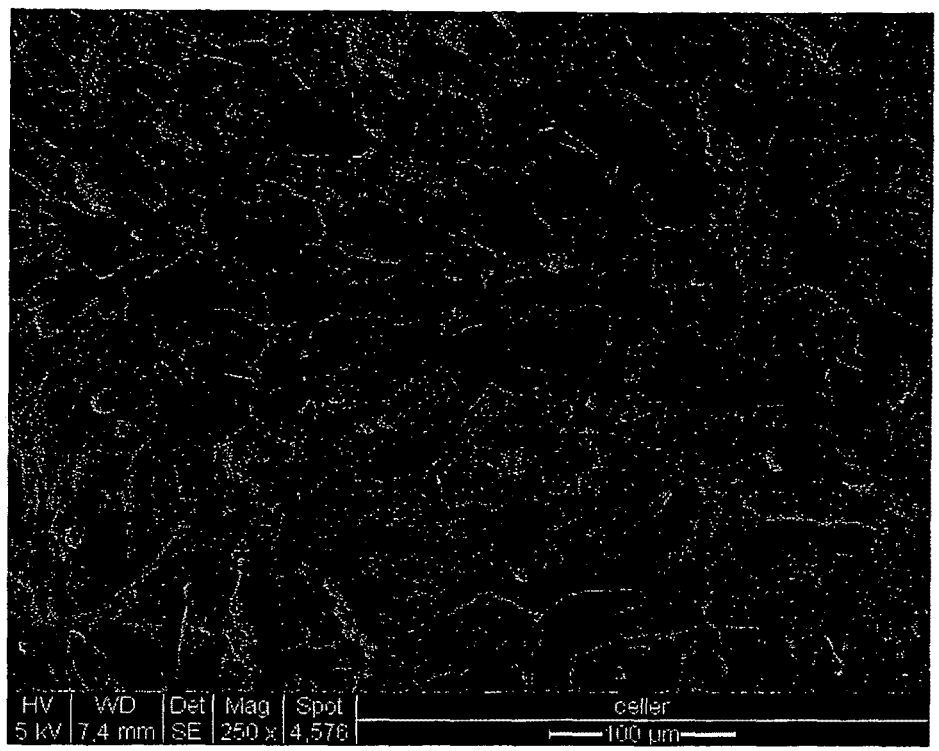
FIG. 20b is a scanning electron microscopy image of cells grown for 36 hours on a surface of a component according to the invention.
Figure 20C:
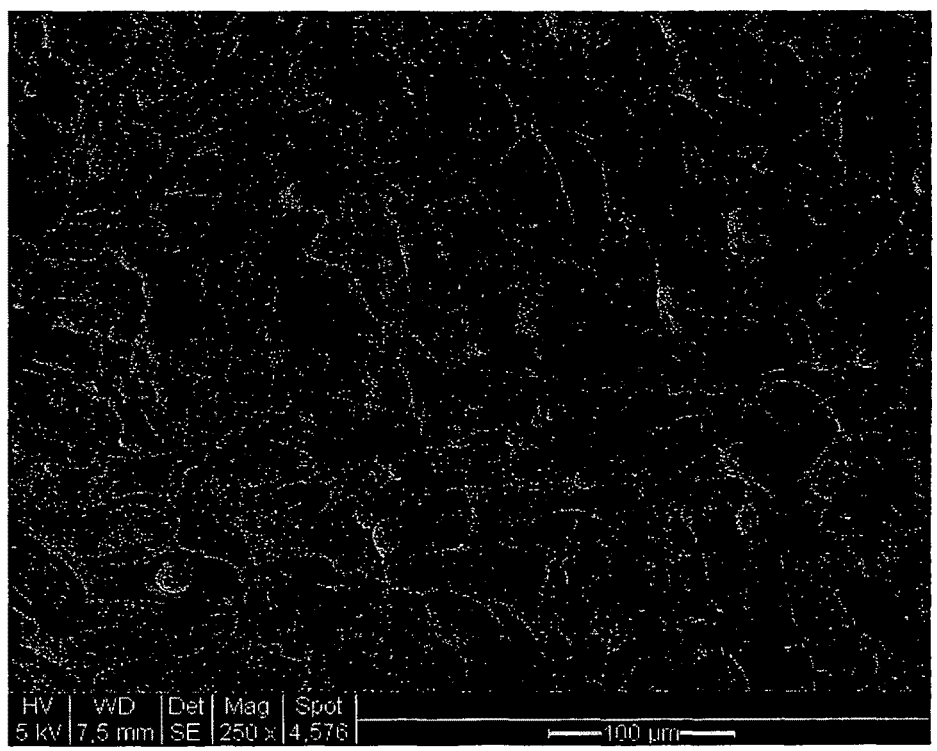
FIG. 20c is a scanning electron microscopy image of cells grown for 36 hours on a surface of a component according to the invention.

In summary, it was found that the samples according to the invention induced a lower cell density and a lower number of adherent cells compared to reference surfaces. However, among the cells grown on the surfaces according to the invention, a higher number of cells were proliferative compared to cells grown on the reference surfaces. Cells grown on the surfaces according to the invention were also less apoptotic, more elongated and had many small projections indicating activity, as is seen in FIG. 20a-c.

Cells grown on both surfaces according to the invention exhibited a significantly increased PGE2 production after 14 days of cultivation compared to that of cells grown on a conventional surface. Furthermore, cells grown on a surface according to the invention comprising a secondary nanostructure had a markedly higher ALP activity than cells grown on a conventional surface. An increase in ALP and/or PGE2 activity is related to an increased osteoblast activity, reduced osteoclast activity and an accelerated mineralization of the ECM. Thus, in conclusion, the invention provides a biocompatible component which is improved in respect of bone formation rate and osseointegration.

Example 3

Implantation

The integration of implants according to the invention was tested in a rabbit model. The objective was to qualitatively and quantitatively study the in vivo bone tissue response to two implant surface modifications according to the invention compared to the response to commercially available reference implants.

(i) Implants for Removal Torque Study

Titanium torque fixtures (square headed removal torque design, 3.5×8.2 mm) prepared by immersion in oxalic acid and subsequently in HF as described in Example 1 (i.e., including steps b and c) were used (referred to as Test implant 2). Also, torque fixtures (3.5×8.2 mm) were used which were prepared by immersion in oxalic acid according to Example 1 (i.e., step c was omitted) (referred to as Test implant 1). Further, torque fixtures (3.5×8.2 mm) representing the commercially available OsseoSpeed™ oral implant were used as reference fixtures.

(ii) Implants for Histological and Histomorphometrical Study

Fixtures of human design of oral implants (3.5×8 mm) prepared as described in Example 1 above were used (Test implant 2). Also, fixtures were used (3.5×8 mm) which were prepared as described in Example 1, except that the HF treatment (i.e., step c) was omitted (Test implant 1). Further, fixtures (3.5×8 mm) representing the commercially available OsseoSpeed™ oral implant were used as reference fixtures.

(iii) Implant Insertion

Twelve mature male New Zealand white rabbits were scheduled for surgery. One rabbit died during initial anaesthesia (#8). The surgery went uneventful. Low speed drilling (1500 rpg for drilling the holes and 20 rpm for implant insertion) was done with continuous NaCl cooling.

One implant (human design of oral implant; 3.5×8 mm) was inserted into each femur chondyle region and 3 implants (square headed removal torque design; 3.5×8.2 mm) were inserted into in each tuburositas tibia. The femur implants were scheduled for histomorphometrical analysis and the tibia implants for removal torque tests.

(iv) Removal Torque Tests

After six weeks the study was terminated and the rabbits were sacrificed. The implants and surrounding tissue were examined. The tibia implants were easy to locate and all of them showed signs of periosteal bone tissue up-growth. The biomechanical test of the implant-bone interface was performed with the removal torque test (RTQ). The RTQ instrument (Detektor AB, Göteborg, Sweden) is an electronic equipment involving a strain gauge transducer used for testing the implant stability (the peak loosening torque in Ncm) in the bone bed and can thus be regarded as a three dimensional test roughly reflecting the interfacial shear strength between bone tissue and the implant (Johansson C. B., Albrektsson T., Clin Oral implants Res 1991; 2:24-9). A linear increasing torque was applied on the same axis of the implant until failure of integration was obtained, and the peak value was noted. The implants inserted in femur more often revealed a "complete coverage" of the implant head with bone tissue. The femur implants were immersed in fixative solution and further processed for histological and histomorphometrical investigations.

Figure 22:
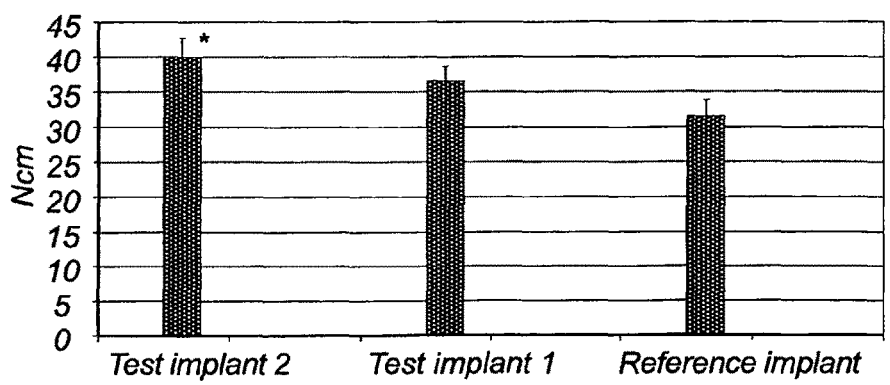
FIG. 22 is a graph showing removal torque test results for implants according to the invention and a commercial titanium implant in a rabbit model.

The mean values of Test implants 1, Test implants 2 and reference implants for removal torque tests are presented in FIG. 22. Comparisons of all Test implants 1, Test implants 2 and reference implants revealed a 25% improvement in removal torque values for Test implants 2 compared to the reference implants. This difference was statistically significant ($p<0.05$; Student T-test). Moreover, the results suggested that the removal torque values of Test implants 1 were equal to or higher than those of the reference implants.

(v) Histological Evaluation

After six weeks the study was terminated and the rabbits were sacrificed. Selected samples of the femur implante site including bone tissue and implant from rabbits #1 and #5 were histomorphometrically evaluated in terms of bone to implant contact (BIC) and bone area inside the inner threads (inner area, ia) and in the corresponding mirror images (mi) in various regions around the implants retrieved from femur.

Mean values for BIC and bone area of different regions of the implant as well as a total mean value for BIC and bone area for each implant are reported in Tables 2 and 3 below. The following implant regions were evaluated:
(a) micro-threads;
(b) macro-threads;
(c) along the apical sides (without threads) in the marrow cavity; and
(d) in the apical bottom of the implant (this region is reported for bone implant contact only)

TABLE 2

Mean values for bone implant contact (BIC) (% of total contact)

| Sample | Micro-threads | Macro-threads | Apical sides | Mean value | Apical bottom | Total mean value incl. bottom |
|---|---|---|---|---|---|---|
| Rabbit #1 Test implant 2 | 14 | 30 | 15 | 20 | 30 | 22 |
| Rabbit #1 Reference | 5 | 3 | 10 | 6 | 9 | 7 |
| Rabbit #5 Test implant 1 | 15 | 7.5 | 23 | 15 | 7 | 13 |
| Rabbit #5 Reference | 14 | 19 | 15 | 16 | 21 | 17 |

TABLE 3

Mean values of bone area (% of total area)

| Sample | Micro-threads (ia/mi) | Macro-threads (ia/mi) | Apical sides (ia/mi) | Mean value (ia/mi) |
|---|---|---|---|---|
| Rabbit #1 Test implant 2 | 29/35 | 29/31 | 69/43 | 42/36 |
| Rabbit #1 Reference | 13/26 | 10/8 | 29/10 | 17/15 |
| Rabbit #5 Test implant 1 | 34/45 | 9/6 | 48/4 | 30/18 |
| Rabbit #5 Reference | 36/35 | 25/17 | 6/10 | 22/31 | ia = inner area,
mi = mirror image

Figure 24A:
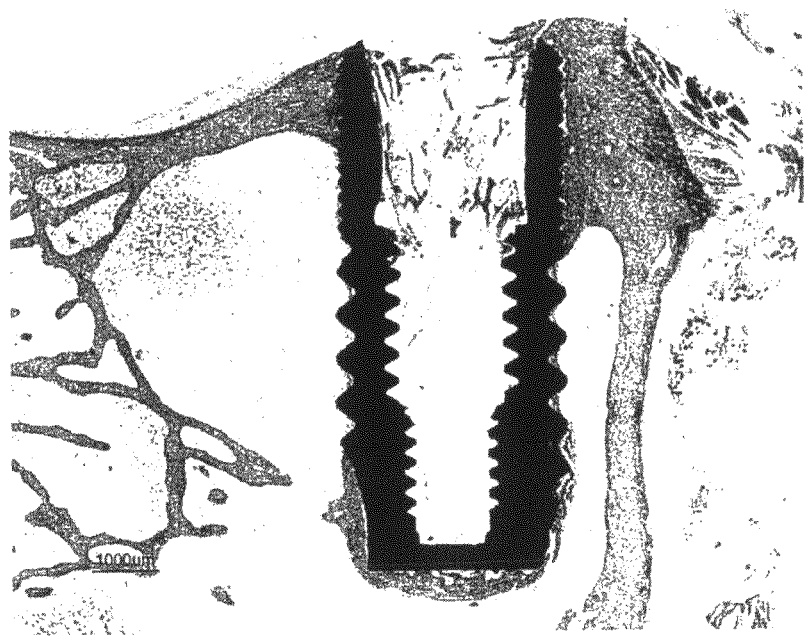
FIG. 24a-b are histology section images of an implant according to the invention and a commercial titanium implant, respectively, in a rabbit model six weeks after implantation.

For rabbit #5, reference implant, the section was accidentally made through the cut present in all implants. For this sample, the calculated bottom contact distance was based on an approximation of the total distance of that of rabbit #3, Test implant 1 (FIG. 24a).

Figure 23A:
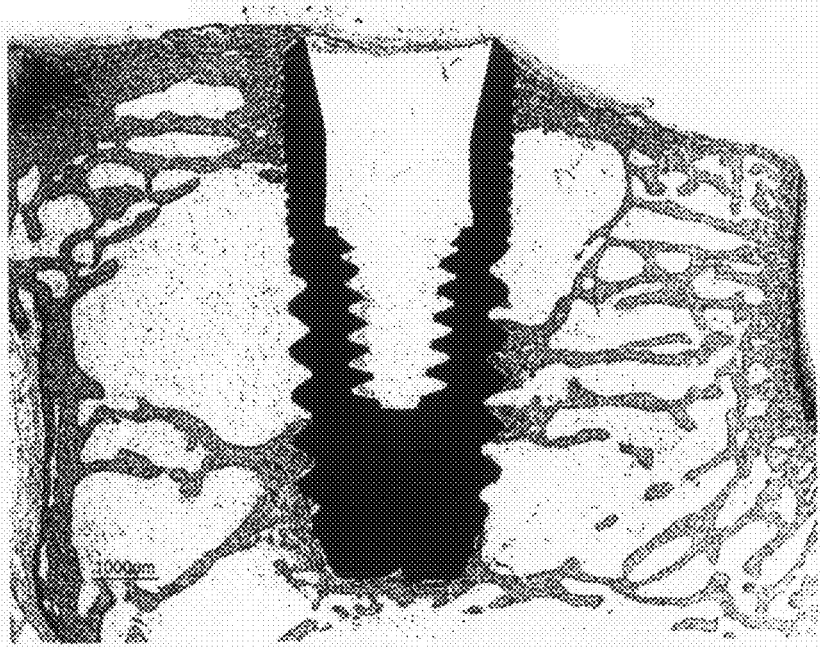
FIG. 23a-b are histology section images of an implant according to the invention and a commercial titanium implant, respectively, in a rabbit model six weeks after implantation.
Figure 23B:
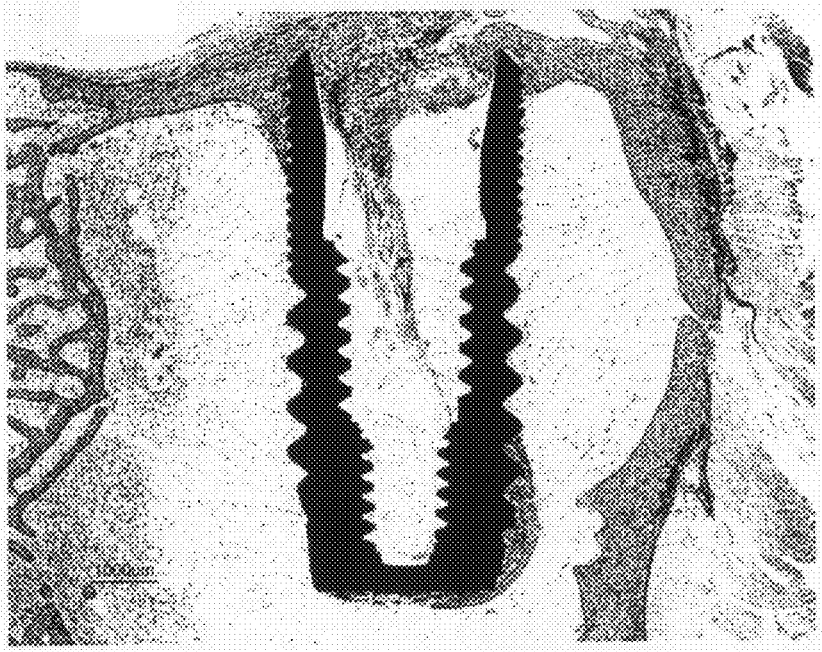
Figure 24B:
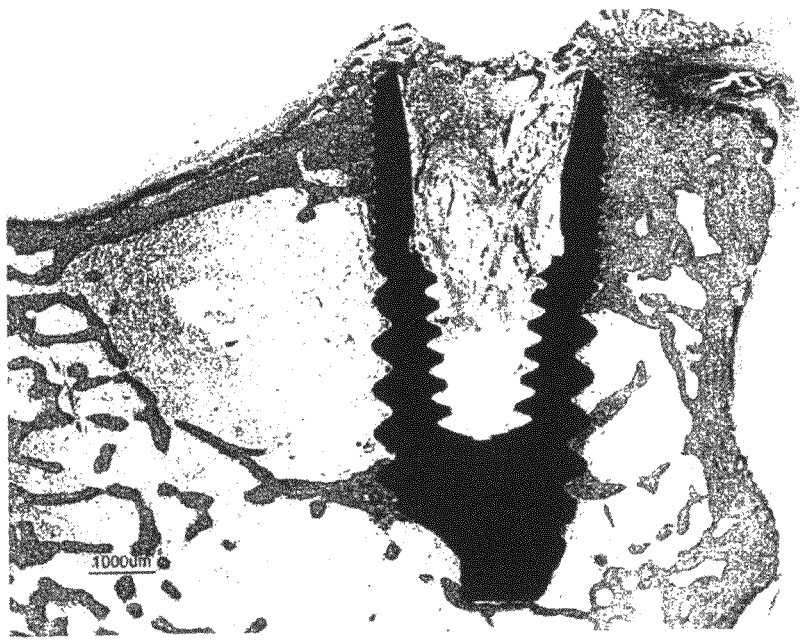

As can be seen in Tables 2 and 3, Test implant 2 showed higher bone implant contact and a larger bone area in the threads compared to the reference surface. Test implant 1 showed almost equal bone implant contact compared to the reference surface. Also, a larger inner bone area in the threads compared to that of the reference implant was observed (Table 2). Histology sections images qualitatively showing bone formation are presented in FIGS. 23-24, in which
FIG. 23a represents rabbit #1, Test implant 2;
FIG. 23b represents rabbit #1, reference implant;
FIG. 24a represents rabbit #5, Test implant 1; and
FIG. 24b represents rabbit #5, reference implant.

Nearly all samples revealed more newly formed bone than old bone in close relation to the implant in the upper micro-threaded region. The bone tissue observed in the macro-threads, in the non threaded sides of the implant in the marrow cavity and in the apical bottom layer was also newly formed.

In rabbit #1, a great amount of ongoing bone formation around Test implant 2 was observed compared to the reference implant. Osteoid seams with osteoblast rims of various shapes of the osteoblasts, were frequently observed (FIG. 23a, b).

In rabbit #5, a great amount of ongoing bone formation around Test implant 1 compared to the reference implant was observed. Osteoblasts were frequently observed however not as pronounced as around Test implant 2 of rabbit #1 (FIG. 24a, b).

The implant surfaces were in close connection to the fat cells of the marrow cavity irrespective of implant surface, indicating a high degree of biocompatibility of all surfaces with the sensitive bone marrow cells.

Example 4

Apatite Formation In Vitro

One conventional in vitro model for studying bone formation is the immersion of biomaterials in simulated body fluids (SBFs). SBFs are solutions having ion concentrations approximately equal to those of human blood plasma (Kokubo T., Kushitani H., Sakka S., Kitsugi T., Yamamuro T., J Biomed Mater Res 1990; 24: 721-734; Oyane A., Kim H. K., Furuya T., Kokubo T., Miyazaki T., Nakamura T., J Biomed Mater Res 2003; 65A, 188-195). Depending on the nucleating capacity of the biomaterial, bone-like calcium phosphates will precipitate onto its surface. A quantitative correlation of apatite formation in SBF with in vivo bone bioactivity has been reported (Kokubo T., Takadama H., Biomaterials 2006; 27: 2907-2915). Today the SBF in vitro model is frequently used and is described by the international standard ISO 23317:2007 E.

(i) SBF Immersion
A revised SBF (Oyane A. et al, J Biomed Mater Res 2003; 65A, 188-195) having an electrolyte concentration very similar to that of human plasma (Vander A. J., Sherman J. H., Luciano D. S., "Human physiology The mechanisms of body function", 5th ed. McGraw-Hill Publishing Company, New York, 1990: 349-400) was selected. The SBF was prepared by dissolving 10.806 g NaCl, 1.480 g $NaHCO_3$, 4.092 g $Na_2CO_3$, 0.450 g KCl, 0.460 g $K_2HPO_4.3H_2O$, 0.622 g $MgCl_2.6H_2O$, 23.856 g 2-(4-(2-hydroxyethyl)-1-piperazinyl)ethanesulfonic acid (HEPES), 0.776 g $CaCl_2$, and 0.144 g $Na_2SO_4$ in 2000 ml deionised water. HEPES was dissolved in 200 ml deionised water before being added to the solution. The final pH was adjusted to 7.40 at 37° C. with 1.0 M NaOH. All chemicals were obtained from Merck (Sweden), except for NaCl and $Na_2SO_4$ which were obtained from Fluka (Sweden).

Three sets of coin shaped β sterilised titanium samples, one set having been subjected to step b according to the invention (referred to as Inventive surface 1), one set having been subjected to step b and step c according to the invention (Inventive surface 2), and one reference set representing a commercially available surface (OsseoSpeed™; Astra Tech AB, Sweden), were immersed in 37 ml SBF in separate and sealed 50 ml polystyrene vials (VWR, Sweden) at 37° C. The samples were mounted hanging in the lid of the vials, allowing the side of the coin to be analysed to be oriented downwards without being contacted by any other objects. After three days the SBF immersion was interrupted and the samples were thoroughly rinsed with deionised water to remove any loosely attached calcium phosphate material. The samples were then dried at room temperature in a laminar air flow bench. Three samples of each set were not immersed in SBF, thus serving as controls.

(ii) Morphology of Apatite Formed (SEM)

Figure 25A:
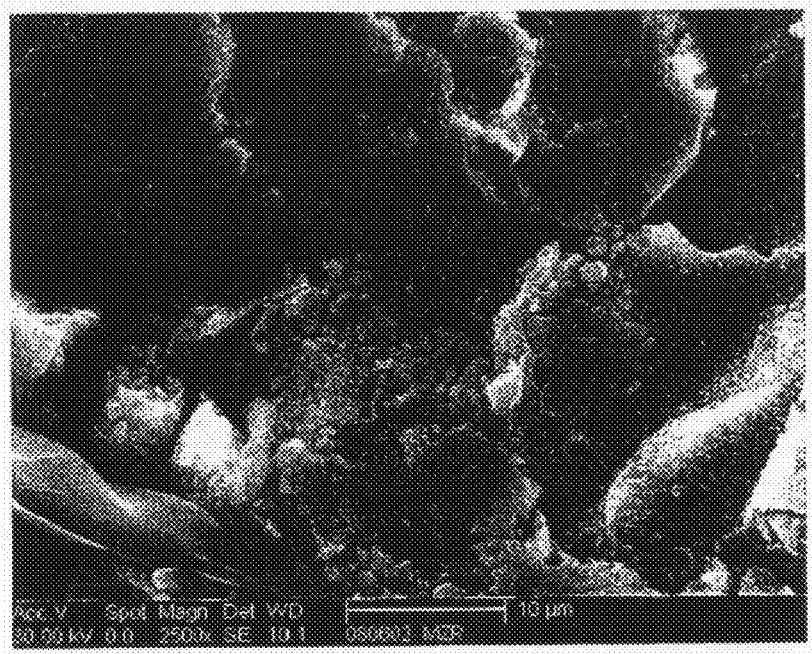
FIG. 25a is a scanning electron microscopy image of a reference titanium sample representing the surface of a commercial titanium implant.
Figure 25B:
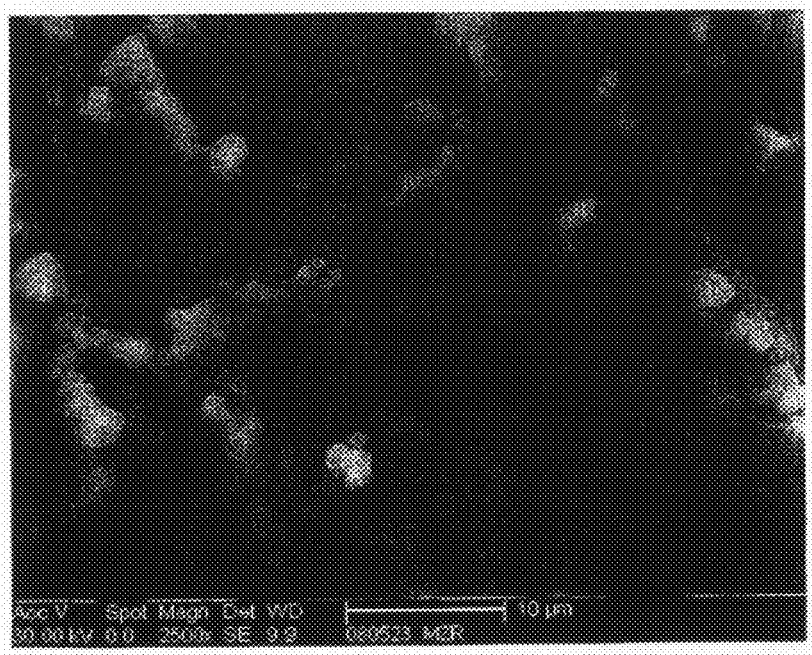
FIG. 25b is a scanning electron microscopy image of the sample shown in FIG. 25a after immersion in simulated body fluid (SBF).
Figure 26A:
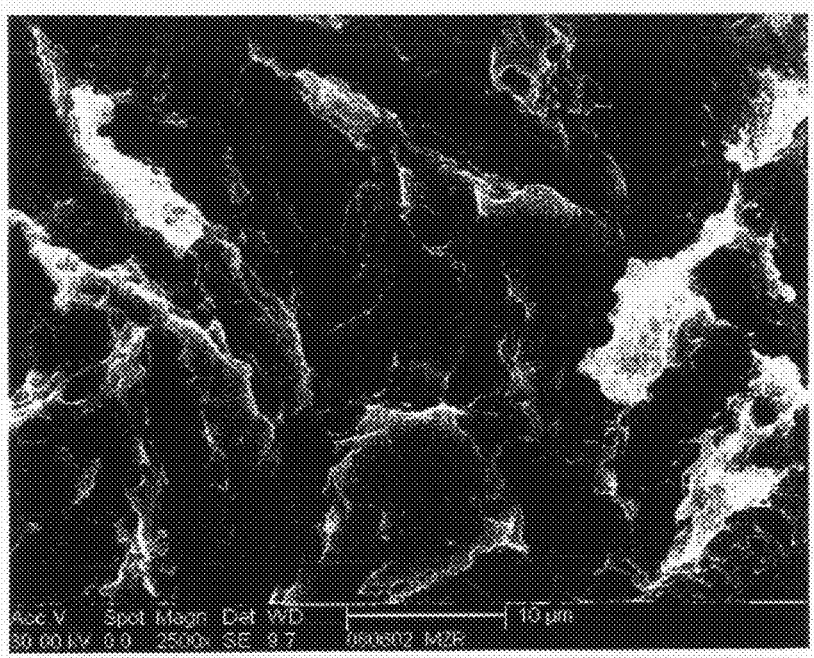
FIG. 26a is a scanning electron microscopy image of a titanium sample treated according to step b of the invention.
Figure 26B:
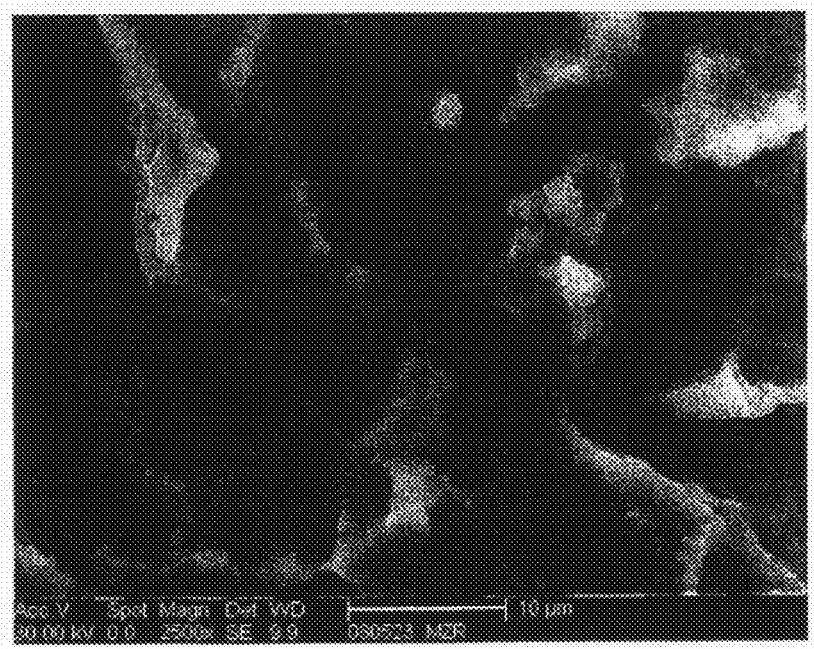
FIG. 26b is a scanning electron microscopy image of the sample shown in FIG. 26a after immersion in simulated body fluid (SBF).
Figure 27A:
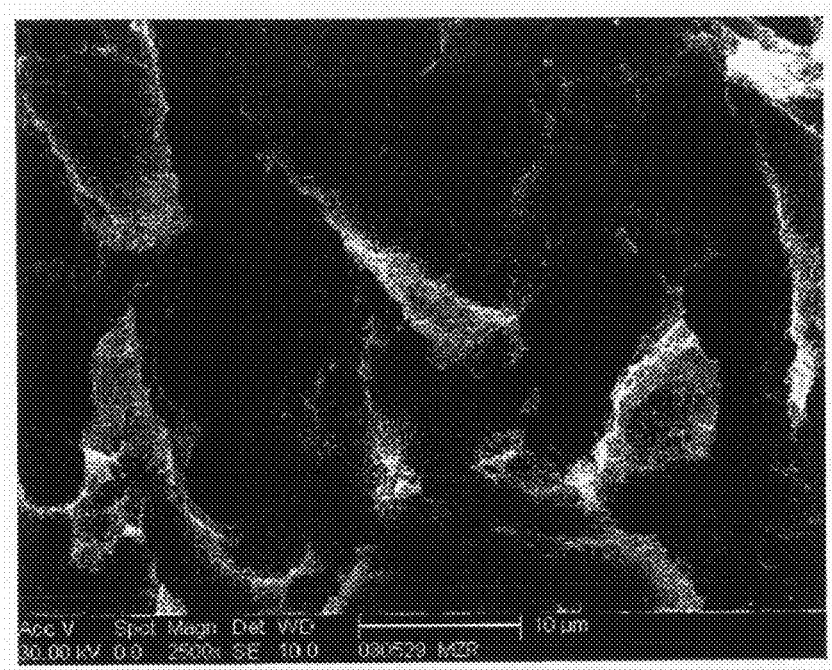
FIG. 27a is a scanning electron microscopy image of a titanium sample treated according to steps b and c of the invention.
Figure 27B:
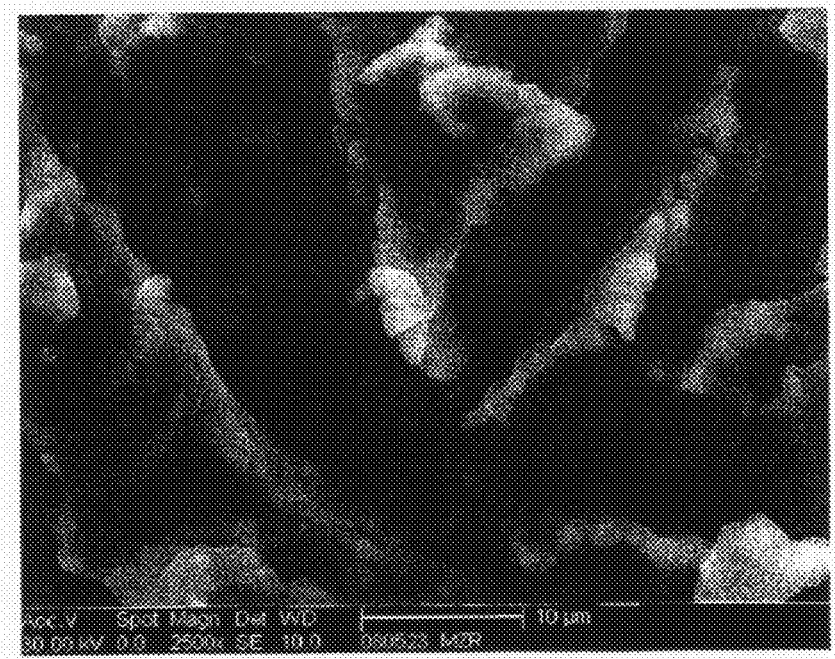
FIG. 27b is a scanning electron microscopy image of the sample shown in FIG. 27a after immersion in simulated body fluid (SBF).

Analyses of possible apatite formation were performed using an environmental scanning electron microscope (ESEM, XL 30, FEI). SEM images of the surface structures before SBF immersion are presented in FIGS. 25a (reference), 26a (Inventive surface 1) and 27a (Inventive surface 2). When the surface structures after SBF immersion were studied, it was concluded that a thin layer of calcium phosphate had been formed on all sets of samples; reference (FIG. 25b), Inventive surface 1 (FIG. 26b) and Inventive surface 2 (FIG. 27b).

(iii) Chemical Evaluation of Apatite Formed (EDS)

Energy dispersive spectroscopy (EDS, Apollo 40, EDAX) was used for chemical analysis of samples before and after apatite formation. By analysing the titanium signal, the degree of coverage of the samples by calcium phosphates could be assessed indirectly. Inventive surface 2 showed the largest decrease in titanium signal (FIG. 28) after SBF immersion, thus indicating the most extensive apatite formation among the sets of samples investigated.

Figure 29:
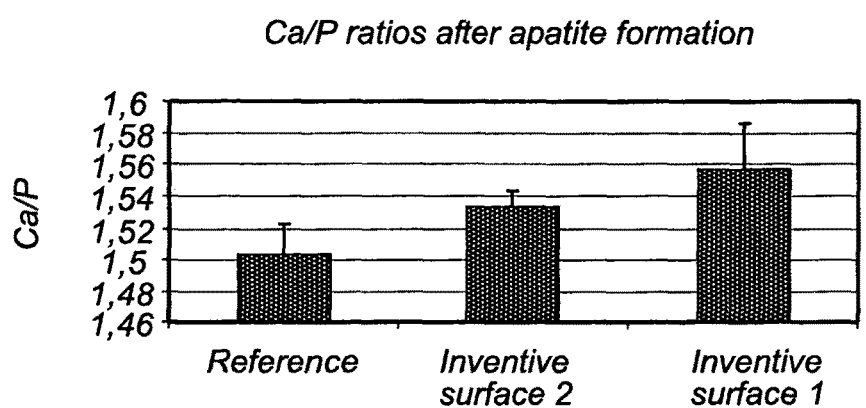
FIG. 29 is a graph presenting the calculated Ca/P ratios after apatite formation of a reference sample and of samples treated according to the invention.

EDS was also used for calculation of the Ca/P ratio in order to estimate the relative prevalence of amorphous and crystalline calcium phosphates. The Ca/P ratios are presented in FIG. 29. The resulting Ca/P ratios indicate a higher degree of crystallinity of apatite formed on the Inventive surface 1 and Inventive surface 2 than on the reference surface. The stoichiometric Ca/P atomic ratios of tricalcium phosphate ($Ca_3(PO_4)_2$), and hydroxyapatite ($Ca_5(PO_4)_3OH$) are 1.5, and 1.67, respectively.

Figure 28:
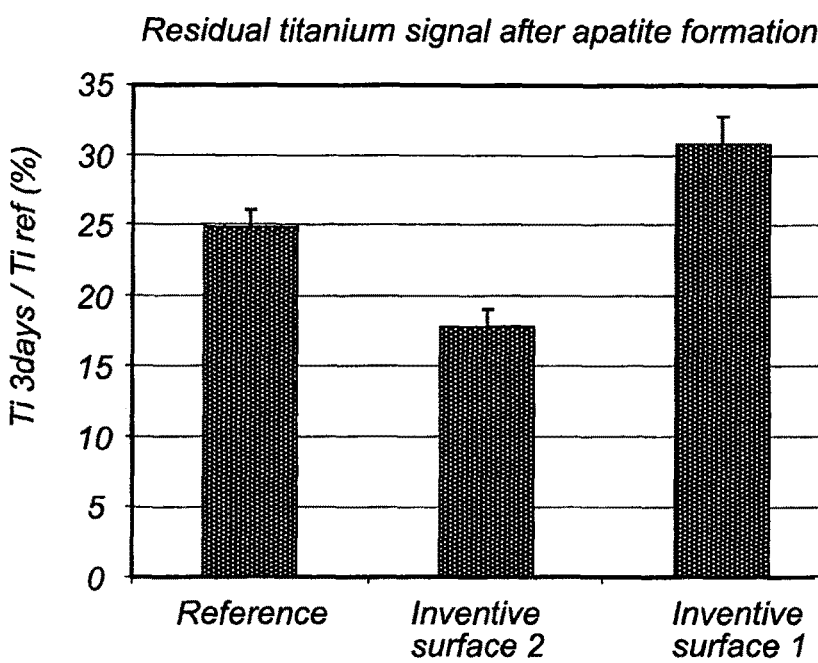
FIG. 28 is a graph showing the residual titanium signal after apatite formation of a reference sample and of samples treated according to the invention as measured by energy dispersive spectroscopy.

In summary, early apatite formation was found on all sets of samples, Inventive surface 2 showing the highest degree of apatite coverage, as concluded by the titanium signal (FIG. 28).

The invention claimed is:

1. A method for modification of a biocompatible component comprising the steps of
    a) providing a biocompatible component at least partly covered by metallic oxide;
    b) treating at least a part of said component, which part is covered by said metallic oxide, with an aqueous composition comprising oxalic acid,
        whereby a reactive metallic oxide is obtained; and
    c) treating at least part of said reactive metallic oxide with a second aqueous composition comprising hydrofluoric acid,
        wherein step c is performed before the reactive metallic oxide becomes passivated.

2. The method according to claim 1, wherein the composition of step b has a concentration of oxalic acid in the range of from 0.001 to 5 M; and the treatment of step b is performed for a treatment time in the range of from 10 to 60 minutes.

3. The method according to claim 2, wherein said treatment time is in the range of from 20 to 30 minutes.

4. The method according to claim 2, wherein the composition of step b has a temperature in the range of from about 20° C. to about 100° C.

5. The method according to claim 1, wherein step c is performed within 180 hours or less after the completion of step b, counted. as the time said component is kept at 0° C. or above and at normal atmospheric pressure in an oxygen-containing atmosphere.

6. The method according to claim 1, wherein step e is performed within 72 hours or less after the completion of step b.

7. The method according to claim 1, wherein step c is performed within 24 hours or less after the completion of step b.

8. The method according to claim 1, wherein step c is performed within 1 hour or less after the completion of step b.

9. The method according to claim 1, wherein step c is performed within 10 minutes or less after the completion of step b.

10. The method according to claim 1, wherein said second aqueous composition has a pH in the range of from 0.5 to 5, a concentration of said hydrofluoric acid in the range of 0.05 to 0.5 M, and the treatment of step c is performed for an active treatment time in the range of from 10 seconds to 3 minutes.

11. The method according to claim 1, wherein said second aqueous composition has a temperature in the range of from 15 to 25° C.

12. The method according to claim 1, wherein said aqueous composition of step b comprises a bone-growth enhancing material.

13. The method according to claim 1, wherein said second aqueous composition comprises a bone-growth enhancing material.

14. The method according to claim 12 or 13, wherein said bone-growth enhancing material comprises metal ions or a salt thereof.

15. The method according to claim 14, wherein said metal ions comprise ions selected from the group consisting of titanium ions, magnesium ions, calcium ions, lithium ions, strontium ions and any combination thereof.

16. The method according to claim 14, wherein said metal ions comprise lithium ions.

17. The method according to claim 14, wherein said metal ions comprise strontium ions.

18. The method according to claim 1, wherein said biocompatible component at least partly consists of titanium or a titanium alloy.

19. The method according to claim 1, wherein said metallic oxide comprises titanium oxide.

20. The method according to claim 1, wherein said metallic oxide consists essentially of a titanium oxide or a combination of titanium oxides.

21. The method according to claim 1, wherein said metallic oxide comprises passivating titanium oxide.

22. The method according to claim 1, wherein said component prior to step b is subjected to a mechanical surface treatment.

23. The method according to claim 22, wherein said mechanical surface treatment comprises blasting.

24. The method according to claim 1, wherein said component prior to step b is subjected to a. chemical surface treatment.

25. The method according to claim 24, wherein said chemical surface treatment comprises a degreasing or cleaning treatment.

26. The method according to claim 1, wherein said biocompatible component is a dental component selected from the group consisting of an implant, a fixture, an abutment, a one-piece implant, or combinations thereof.

27. The method according to claim 1, wherein said biocompatible component is an orthopaedic component.

* * * * *